US011020410B2

(12) United States Patent
Karp et al.

(10) Patent No.: US 11,020,410 B2
(45) Date of Patent: Jun. 1, 2021

(54) SELF-ASSEMBLED GELS FORMED WITH ANTI-RETROVIRAL DRUGS, PRODRUGS THEREOF, AND PHARMACEUTICAL USES THEREOF

(71) Applicant: The Brigham and Women's Hospital, Inc., Boston, MA (US)

(72) Inventors: Jeffrey M. Karp, Brookline, MA (US); Nitin Joshi, Quincy, MA (US); Douglas Rioux, New Haven, CT (US); Nicholas Edward Sherman, Rock Tavern, NY (US); Andrew John Pickering, Brookline, MA (US); Connor Francis Gallin, Boston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 16/482,664

(22) PCT Filed: Feb. 5, 2018

(86) PCT No.: PCT/US2018/016835
§ 371 (c)(1),
(2) Date: Jul. 31, 2019

(87) PCT Pub. No.: WO2018/144991
PCT Pub. Date: Aug. 9, 2018

(65) Prior Publication Data
US 2020/0009164 A1    Jan. 9, 2020

Related U.S. Application Data

(60) Provisional application No. 62/454,212, filed on Feb. 3, 2017.

(51) Int. Cl.
| | | |
|---|---|---|
| A61K 31/675 | (2006.01) | |
| A61K 9/00 | (2006.01) | |
| A61K 9/06 | (2006.01) | |
| A61K 47/14 | (2017.01) | |
| A61K 47/22 | (2006.01) | |
| A61K 47/26 | (2006.01) | |
| A61K 47/28 | (2006.01) | |

(52) U.S. Cl.
CPC .......... *A61K 31/675* (2013.01); *A61K 9/0019* (2013.01); *A61K 9/06* (2013.01); *A61K 47/14* (2013.01); *A61K 47/22* (2013.01); *A61K 47/26* (2013.01); *A61K 47/28* (2013.01)

(58) Field of Classification Search
CPC ............................... A61K 31/675; A61K 9/06
USPC ......................................................... 514/76
See application file for complete search history.

(56) References Cited

U.S. PATENT DOCUMENTS

| | | |
|---|---|---|
| 5,603,959 A | 2/1997 | Horrobin |
| 6,031,017 A | 2/2000 | Waki |
| 6,471,970 B1 | 10/2002 | Fanara |
| 7,749,485 B2 | 7/2010 | Tournier |
| 9,452,178 B1 | 9/2016 | Hauser |
| 9,962,339 B2 | 5/2018 | Karp |
| 2005/0084470 A1 | 4/2005 | Abbas |
| 2005/0220822 A1 | 10/2005 | Hoffman |
| 2005/0267036 A1 | 12/2005 | Garry |
| 2005/0287198 A1 | 12/2005 | Murthy |
| 2006/0276676 A1 | 12/2006 | van Bommel |
| 2008/0004398 A1 | 1/2008 | Durrieu |
| 2008/0021068 A1 | 1/2008 | Alam |
| 2008/0038316 A1 | 2/2008 | Wong |
| 2009/0048296 A1 | 2/2009 | Campbell |
| 2009/0110735 A1 | 4/2009 | Maggio |
| 2009/0169498 A1 | 7/2009 | de Jong |
| 2009/0257968 A1 | 10/2009 | Walton |
| 2009/0263489 A1 | 10/2009 | Zanella |
| 2010/0129451 A1 | 5/2010 | John |
| 2011/0229565 A1 | 9/2011 | Karp |
| 2012/0022158 A1 | 1/2012 | Niu |
| 2012/0189588 A1 | 7/2012 | Nahas |
| 2013/0079371 A1 | 3/2013 | Sundberg |
| 2013/0273140 A1 | 10/2013 | Maggio |
| 2013/0280334 A1 | 10/2013 | Karp |
| 2013/0309286 A1 | 11/2013 | Engstad |
| 2014/0302144 A1 | 10/2014 | Koutsopoulos |
| 2015/0125403 A1 | 5/2015 | Joerger |
| 2015/0202586 A1 | 7/2015 | Imoto |

(Continued)

FOREIGN PATENT DOCUMENTS

| | | |
|---|---|---|
| AU | 2015200633 | 2/2015 |
| EP | 0517211 | 12/1992 |

(Continued)

OTHER PUBLICATIONS

Jibry, et. al., Journal of Pharmacy and Pharmacology (2006), 58(2), 187-194.*
Bell, et al., "Self□assembling peptides as injectable lubricants for osteoarthritis", Journal of Biomedical Materials Research, 78A (2):236-246 (2006).
Bennett, et al., "Next-generation hydrogel films as tissue sealants and adhesion barriers", Cardiac Surgery, 18:494-9 (2003).
Bhattacharya, et al., "Advances in Molecular Hydrogels", Molecular Gels. Materials with Self-Assembled Fibrillar Networks, 17:613-647 (2004).

(Continued)

*Primary Examiner* — Jeffrey H Murray
(74) *Attorney, Agent, or Firm* — Pabst Patent Group LLP

(57) ABSTRACT

Self-assembled gels and methods of making thereof are described. A selective range of ratios between an organic solvent and optionally water, or an aqueous solution, allows for combinations of gelators (such as GRAS amphiphiles or prodrug-based gelators), co-gelators (such as anti-retrovirals), and solvents to form self-supporting hydrogels or organogels. The resulting gels may be used in methods of treating HIV and/or hepatitis.

10 Claims, 5 Drawing Sheets

(56) References Cited

U.S. PATENT DOCUMENTS

| | | | |
|---|---|---|---|
| 2015/0297731 | A1 | 10/2015 | Chiou |
| 2016/0243026 | A1 | 8/2016 | Pathak |
| 2017/0000888 | A1 | 1/2017 | Karp |
| 2017/0100342 | A1 | 4/2017 | Karp |
| 2017/0319500 | A1 | 11/2017 | Karp |
| 2018/0000935 | A1 | 1/2018 | Parshad |
| 2018/0037634 | A1 | 2/2018 | Viswanathan |
| 2018/0050055 | A1 | 2/2018 | Ahmed |

FOREIGN PATENT DOCUMENTS

| | | |
|---|---|---|
| EP | 1063007 | 12/2000 |
| EP | 2361640 | 8/2011 |
| FR | 2417494 | 9/1979 |
| WO | 9907416 | 2/1999 |
| WO | 2003006043 | 1/2003 |
| WO | 2005056039 | 6/2005 |
| WO | 2006008386 | 1/2006 |
| WO | 2010033726 | 3/2010 |
| WO | 2012040623 | 3/2012 |
| WO | 2014041378 | 3/2014 |
| WO | 2014089472 | 6/2014 |
| WO | 2017186928 | 11/2017 |
| WO | 2017193138 | 11/2017 |
| WO | 2017193139 | 11/2017 |
| WO | 2018007327 | 1/2018 |
| WO | 2018015539 | 1/2018 |
| WO | 2018031954 | 2/2018 |
| WO | 2018039247 | 3/2018 |

OTHER PUBLICATIONS

Bhuniya, et al., "(S)-(+)-Ibuprofen-Based Hydrogelators: An Approach Toward Anti-Inflammatory Drug Delivery", Tetrahedron Lett., 47:7153-6 (2006).

Bong, et al., "Self-Assembling Organic Nanotubes," Agnew. Chem. Int. Ed., 40:988-1011 (2001).

Bonte and Juliano, "Interactions of liposomes with serum proteins", Chem. Phys. Lipids, 40:359-72 (1986).

Boutaud, et al., J.A. "Determinants of the Cellular Specificity of Acetaminophen as an Inhibitor of Prostaglandin H(2) Synthases", PNAS, 99:7130-5 (2002).

Browne, et al., "Clinical outcome of autologous chondrocyte implantation at 5 years in US subjects", Clin. Orthop. Relat. Res., 436:237-45 (2005).

Bryers, et al., "Biodegradtion of Poly(anhydride-esters) into Non-Steroidal Anti-Inflammatory Drugs and Their Effect on Pseudomonas aeruginosa Biofilms In Vitro and on the Foreign-Body Response In Vivo," Biomaterials, 27:5039-48 (2006).

Burns, et al., "Physical characterization and lipase susceptibility of short chain lecithin/triglycer mixed micelles potential lipoprotein models", J. Biol. Chem., 256(6):2716-22 (1981).

Caran, et al., "Anatomy of a Gel. Amino Acid Derivatives that Rigidity Water at Submillimolar Concentrations," Am. Chem. Soc., 122: 11679-11691 (2002).

Casuso, et al., "Converting drugs into gelators: supramolecular hydrogels from N-acetyl-L-cysteine and coinage-metal salts", Org. Biomol. Chem., 8:5455-8 (2010) (Abstract Only).

Choi, et al., "Studies on gelatin-based sponges. Part III: A comparative study of cross-linked gelatin/alginate, gelatin/hyaluronate and chitosan/hyaluronate sponges and their application as a wound dressing in full-thickness skin defect of rat", J. Materials Sci., 12:67-73 (2001).

Chourasia, et al., "Pharmaceutical Approaches to Colon-Targeted Drug Delivery Systems", Pharm. Pharmaceut. Sci., 6:22-66 (2003).

Donati, et al., "Synergistic effects in semidilute mixed solutions of alginate and lactose-midified chitosan (chitlac)", Biomacromolecules, 8:957-62 (2007).

Erdmann, et al., "Degradable Poly(anhydridie ester) Implants: Effects of Localized Salicylic Acid Release on Bone", Biomaterials, 21:2507-12 (2000).

Estroff, et al., "Effective Gelation of Water Using a Series of Bis-urea Dicarboxylic Acids", Angew. Chem. Int. Ed., 39:3447-50 (2000).

European Search Report for EP 11827647 dated Jul. 16, 2014.

Fischel-Ghodsian, et al., "Enzymatically Controlled Drug Delivery", PNAS, 85:2403-6 (1988).

Friggeri, et al., "Entrapment and release of quinoline derivatives using a hydrogel of a low molecular weight gelator", Controlled Release, 97:241-8 (2004).

Gong, et al., "Synthesis ofhydrogels with extremely low surface friction", J. Am. Chem. Soc., 123:5582 (2001).

Gopinath, et al., "Ascorby1 palmitate vesicles (aspasomes): formation characterization and applications", Intl. J. Pharma., 271(1-2):95-113 (2004).

Gupta, et al., "Hydrogels.from controlled release to pH-responsive drug delivery", Drug Discovery Today, 7:569-79 (2002).

Han, et al., "Catalytic ester-amide exchange using group (iv) metal alkoxide-activator complexes", JACS, 127:10039-44 (2005).

Hans, et al., "Synthesis and characterization ofmPEG-PLA prodrug micelles", Biomacromolecules, 6:2708-17 (2005).

Harten, et al., "Salicylic acid-derived poly(anhydride-esters) inhibit bone resorption and formation in vivo", Biomed. Mater. Res-A, 72A:354-62 (2005).

Higuchi, et al., "Specificity of Esterases and Effect of Structure of Prodrug Esters od Acylated Acetaminophen on Hyrdolytic Reactivity", Pharmacokinetics, 9:67-82 (1984).

Hoare, et al., "Hydrogelsin drug delivery: Progress and challenges", Polymer, 49:1993-2007 (2008).

Huang, et al., "On the importance and mechanisms of burst release in matrix-controlled drug delivery systems", Controlled Release, 73: 121-36 (2001).

Hunziker, "Articular cartilage repair: basic science and clinical progress. A review of the current status and prospects", Osteoarthritis Cartilage, 10:432-63 (2002).

Indomethacin, MSDS product information, copyright Jun. 19, 2012.

International Search Report for corresponding PCT application PCT/US2018/016835 dated Jul. 12, 2018.

International Search Report for PCT/US2016/056070 dated Jan. 12, 2017.

International Search Report for PCT/US2017/031614 dated Jul. 26, 2017.

International Search Report for PCT/US2017/031615 dated Sep. 25, 2017.

International Search Report for PCT/US2018/031654 dated Aug. 8, 2018.

International Search Report for PCT/US2019/025782 dated Jun. 26, 2019.

Jen, et al., "Review: Hydrogels for cell immobilization", Biotechnol. Bioeng., 50:357-64 (1996).

John, et al., "Biorefinery a design tool for molecular gelators," Langmuir. 26: 17843-51 (2010).

John, et al., "Enzymatically Derived Sugar-Containing Self-Assembled Organogels with Nanostructured Morphologies", Agnew. Chem. Int. Ed., 45:4772-5 (2006).

John, et al., "Lipid-based nanotubes as functional architectures with embedded fluorescence and recognition capabilities", J. Am. Chem. Soc., 126:15012-3 (2004a).

John, et al., "Morphological control of helical solid bilayers in high-axial-ratio nanostructures through binary self-assembly", Chem. Eur. J., 8:5494-500 (2002).

John, et al., "Nanotube Formation from Renewable Resources via Coiled Nanofibers", Adv. Mater., 13:715-8 (2001).

John, et al., "Unsaturation effect on gelation behavior ofaryl glycolipids", Langmuir, 20:2060-5 (2004b).

Jovanovic, et al., "How curcumin works preferentially with water soluble antioxidants", Chem. Soc., 123:3064-68 (2001).

Jung, et al., "Self-Assembly ofa Sugar-Based Gelator in Water. Its Remarkable Divers ity in Gelation Ability and Aggregate Structure," Lanumuir, 17:7229-32 (2001).

Kalgutkar, et al., "Ester and Amide Derivatives of the Nonsteriodal Antiinflammatory Drug,Indomethacin, as selective cyclooxvgenase-2 inhibitors," J. Med. Chem., 43:2860-70 (2000).

(56) References Cited

OTHER PUBLICATIONS

Kamath, et al., "Biodegradable Hydrogels in Drug Delivery," Adv. Drug Deliv. Rev., 11:59-84 (1993).

Kaplon, et al., "Antibodies to watch in 2018", MAbs, 10(2):183-203 (2018).

Karim, et al., "Effectiveness and Safety of Tenofovir Gel, and Antiretroviral Microbicide, for the Prevention of HIV Infection in Women", Science, 329:1168-1174 (2010).

Kim, et al., "In vivo evaluation of polymeric micellar paclitaxel formulation. toxicity and efficacy", Controlled Release, 72:191-202 (2001).

Kitagawa, et al., "Cationic Vesicles Consisting of 1, 2-Dioleoyl-3-Trimethylammonium Propane (DOTAP) and Phosphatidylcholines and Their Interaction with Erythrocyte Membrane", Chem. Pharma. Bull., 52(4):451-3 (2004).

Kiyonakam, et al., Semi-wet peptide/protein array using supramolecular hydrogel, Nat. Mater., 3:58-64 (2004).

Kobayashi, et al., "Molecular design of "super" hydrogelators: understanding the gelation process of azobenzene-based sugar derivatives in water", Org. Lett., 4(9): 1423-1426 (2002).

Kohane, et al., "A re-examination of tetrodotoxin for prolonged duration local anesthesia", Anesthesiology, 89(1):119-131 (1998).

Krog et al., "Food emulsifiers: their chemical and physical properties", Food Emulsions, 4:45FF, (2004).

Kumar, et al., "First snapshot ofa nonpolymeric hydrogelator interacting with its getting solvents", Chem. Commun., 4059-62 (2005).

Kumar, et al., "Prodrugs as self-assembled hydrogels: a new paradigm for biomaterials", Biotech., 24:1-9 (2013).

Lee, et al., "Hydrogels for Tissue Engineering," Chem. Rev., 101:1869-80 (2001).

Li, et al., "Thermosensitive hydrogel of hydrophobically-modified methylcellulose for intravaginal drug delivery", J. Mater. Sci: MAter Med., 23:1913-1919 (2012).

Li, et al., "Molecular nanofibers of olsalazine form supramolecular hydrogeis for reductive release of an anti-inflammatory agent", JACS, 132:17707-9 (2010).

Loos, et al., "Design and Application of Self-Assembled Low Molecular Weight Hydrogels," Eur. J. of Organic Chem., 17:3615-31 (2005).

Lu, et al., "Photopolymerization of multilaminated poly (HEMA) hydrogels for controlled release", J. Controlled Release, 57:291-300 (1999).

Luboradzki, et al., "An Attempt to Predict the Gelation Ability of Hydrogen-Bond-Based Gelators Utilizing a Glycosidase Library," Tetrahedron, 56:9595-9 (2000).

Magnussen, et al., "Treatment of focal articular cartilage defects in the knee: a systematic review", Clin. Orthop. Relat. Res., 466:952-96 (2008).

Mahalingam, et al., "Design of a Semisolid Vaginal Microbicide Gel by Relating Composition to Properties and Performance", Pharm. Res., 27:2478-2491 (2010).

Makarevic et al., "Bis(amino acid) oxalyl amides as ambidextrous gelators of water and organicsolvents. supramolecular gels with temperature dependent assembly/dissolution equilibrium", Chem. Eur. J., 7:3328-3341 (2001).

Marsich, et al., "Alginate/lactose-modified chitosan hydrogels: A bioactive biomaterial for chondrocyte encapsulation", J. Biomat. Mater. Res. A, 84(2):364-76 (2008).

Mazumdar, et al., "Preparation and evaluation ofethambutol derivatives", Indian J. Pharm. Sci., 47:179-80 (1985).

Menger, et al., "Anatomy ofa Gel. Amino Acid Derivatives that Rigidify Water at Submillimolar Concentrations", J. Am. Chem. Soc., 122:11679-91 (2000).

Miyata, et al., "Biomolecule-Sensitive ydrogels", Adv. Drug Deliv. Rev., 54:79-98 (2002).

Molinier, et al., "PFGSE-NMR study of the self-diffusion of sucrose fatty acid monoesters in water", J. Colloid Interface Sci., 286(1):360-8 (2005).

Nicolaou, et al., "A Water-Soluble Prodrug of Taxol with Self-Assembling Properties", Agew.Chem. Int. Ed., 33: 1583-7 (1994).

Nishimura, et al., "Analysis of reducing end-groups produced by enzymatic scission of glycoside linkages in O-methylcellulose", Carbohydrate Res., 267:291-8 (1995).

Oda, et al., "Gemini Surfactants as New, Low Molecular Weight Gelators of Organic Solvents and Water", Angew. Chem. Int. Ed., 37:2689-91 (1998).

Palma, et al., "Evaluation of the surfactant properties of ascorbyl palmitate sodium salt", Eu. J. Pharma. Sci., 16(1-2):37-43 (2002).

Peppas, "Hydrogels and Drug Delivery," Curr. Opin. Colloid Interface Sci., 2:531-7 (1997).

Peppas, et al., "Hydrogels in Biology and Medicine. From Molecular Principles to Bionanotechnology", Adv. Mater., 18:1345-1360 (2006).

Peppas, et al., "Hydrogels in pharmaceutical formulations", Eur. J. Pharm. Biopharm., 50:27-46 (2000).

Persico, et al., "Effect of tolmetin glycine amide (McN-4366) a prodrug of tolmetin sodium on adjuvant arthritis in the rat", J. Pharma. Exp. Therap., 247(3):889-96 (1988).

Pietzyk, et al., "Degradation of phosphatidylcholine in liposomes containing carboplatin in dependence on composition and storage conditions", Intl. J. Pharma., 196(2):215-8 (2008).

Poulsen, et al., "Effect of topical vehicle composition on the in vitro release of fluocinolone acetonide and its acetate ester", J Pharma Sci., 57(6):928-33 (1968).

Qiu, et al., "Environment-sensitive hydrogels for drug delivory", Adv. Drug Deliv. Rev., 53:321-39 (2001).

Rajabalaya, et al., "Studies on effect of plasticizer on invitro release and exvivo permeation from eudragit e100 based chlorpheniramine maleate matrix type transdermal delivery system", J. Excipients Food Chem., 1(2):1-12 (2010).

Rattie, et al., "Acetaminophen Prodrugs III. Hydrolysis of Carbonate and Carboxylic Acid Esters in Aqueous Buffers", J. Pharm. Sci., 59:1738-41 (1970).

Robinson, et al., "Design, synthesis, and biological evaluation of angiogenesis inhibitors Aromatic enone and dienone analogues of curcumin", Bioru. Med. Chem. Lett., 13:115-17 (2003).

Rooseboom, et al., "Enzyme-catalyzed activation of anticancer prodrugs", Pharmacol. Rev., 56:53-102 (2004).

Scogs, substances list, http://www.fda.gov/Food/IngredientsPackagingLabeling/GRAS/SCOGS/ucm084104. Retrieved from interner Apr. 3, 2014.

Sinha, et al., "Microbially triggered drug delivery to the colon", Eur. J. Pharm. Sci, 18:3-18 (2003).

Sreenivasachary, et al., "Gelation-driven component selection in the generation of constitutional dynamic hydrogels based on guanine-quartet formation", PNAS, 102:5938-43 (2005).

Szuts, et al., "Study of thermos-sensitive gel-forming properties of sucrose stearates", J Excipients Food Chem., 1(2):13-20 (2010).

Thoughtco. Phosphate-Buffered Saline or PBS Solution Jun. 4, 2018. https://www.thoughtco.com/phosphate-buffered-saline-pbs-solution-4061933 (2018).

Tomsic, et al., "Internally self-assembled thermoreversible gelling mulsions:ISAsomes in methylcellulose, k-carragrrnan, and mixed hydrogels", Langmuir, 25:9525 (2009).

Toth, et al., "Commonly used muscle relaxant therapies for acute low back pain: A review of carisoprodol cyclobenzaprine hydrochloride, and metaxalone", Clin. Therap., 26(9):1355-67 (2004).

Trouet, et al., "Extracellularly tumor-activated prodrugs for the selective chemotherapy of cancer application to doxorubicin and preliminary in vitro and in vivo studies", Cancer Res., 61: 2843-6 (2001).

Troung, et al., "Self assembled gels for biomedical applications", Focus Rev., 6:30-42 (2011).

Ullrich, et al., "Sucrose ester nanodispersions: Microviscosity and viscoelastic properties", Eu. J. Pharma. Biopharma., 70:550-5 (2008).

Vallecillo, "A liquid crystal of ascorbyl palmitate, used as a vaccine platform, provides sustained release of antigen and has intrinsic pro-inflammatory and adjuvant activities which are dependent on MyD88 adaptor protein", Journal of Controlled Release, 214:12-22 (2015).

Van Bommel, et al., "Two-stage enzyme mediated drug release from LMWG gydrogels," Org.Biomol. Chem., 3:2917-2920 (2005).

(56) References Cited

OTHER PUBLICATIONS

Van Der Linden, et al., "Stimulus-sensitive hydrogels and their applications in chemical (micro) analysis", Analyst, 128:325-31 (2003).
Van Esch, et al., "New functional materials based om self-assembling organogels: from serendipity towards design", Angew. Chem. Int., 39:2263-66 (2000).
Vassilev, et al., "Enzymatic Synthesis of a Chiral Gelator with Remarkably Low Molecular Weight", Chem. Commun., 1865-6 (1998).
Vemula et al., "Enzyme catalysis: Tool to make and break amygdalin hydrogelators from renewable resources. A delivery model for hydrophobic drugs", J. Am. Chem. Soc., 128:8932-8 (2006a).
Vemula et al., "Smart Amphiphiles. Hydro/Organogelators for In Situ Reduction of Gold", Chem.Commun., 2218-2220 (2006b).
Vemula, et al., "In Situ Synthesis of Gold Nanoparticles using Molecular Gels and Liquid Crystals from Vitamin-C Amphiphiles", Chem. Mater., 19:138-40 (2007).
Vigroux, et al., "Cyclization-activated prodrugs: N-(substituted 2-hydroxyphenyl and 2-hydroxypropyl) carbamates based on ring-opened derivatives of active benzoxazolones and oxazolidinones as mutual prodrugs of acetaminophen", J. Med. Chem., 38:3983-94 (1995).
Vinson, et al., "Direct Imaging of Surfactant Micelles, Vesicles, Discs, and Ripple Phase Structures by Cryo-Transmission Electron Microscopy", Journal of Colloid and Interface Science, 142(1):74-91 (1991).
Vohra, et al., "Nanolipid carrier-based thermoreversible gel for localized delivery of docetaxel to breast cancer", Cancer Nanotechnol., 4(1-3):1-12 (2013).
Wang, et al., "Low Molecular Weight Organogelators for Water," Chem. Commun., 310-11 (2003).
Wang, et al., "Hydrogels as separation agents, Responsive Gels. Volume Transitions II", Advances in Polymer Science, 67-79 (1993). (Abstract Only).
Whitesides, et al., "Beyond molecules. self-assembly of mesoscopic and macroscopic components", PNAS, 99:4769-74 (2002).
Xing, et al., "Hydrophobic Interaction and Hydrogen Bonding Cooperatively Confer a Vancomycin Hydrogel. A Potential Candidatefor Biomaterials", J. Am. Chem. Soc., 124:14846-7 (2002).
Yan, et al., "Enzymatic Production of sugar Fatty Acids Esters," PhD thesis, University of Stuttgard, (2001).
Yang, et al., "A simple visual assay based on small molecule hydrogels for detecting inhibitors of enzymes," Chem. Commun., 2424-25 (2004).
Yang, et al., "Enzymatic Formation of Supramolecular Hydrogels," Adv. Mater., 16:1440-4 (2004b).
Yang, et al., "Enzymatic Hydrogelation of small Molecules", Ace. Chem. Res., 41:315-26 (2008).
Yang, et al., "Small Molecule Hydrogels Based on a Class of Anti-Inflammatory Agents", Chem. Commun., 208-9 (2004c).
Yang, et al., "Using a Kinase/Phosphatase Switch to Regulate a Supramolecular Hydrogel and Forming the Supramolecular Hydrogel In Vivo", J. Am. Chem. Soc., 128:3038-43 (2006).
Zhang and Weiss, "Self-assembled networks and molecular gels derived from long-chain, naturally-occurring fatty acids", J Brazilian Chem Soc., 27(2):239-55 (2015).
Zhang, et al., "An inflammation-targeting hydrogel for local drug delivery in inflammatory bowel disease", Sci. Transl. Med., 7(300):300ra128 (2015).
Zhang, et al., "Hydrogels: Wet or Let Die", Nature Materials, 3:7-8 (2004).
Zhang, et al., "Self-assembled networks and molecular gels derived from long-chain, naturally-occurring fatty acids", J. Brazilian Chem. Soc., 239-55 (2016).
Zhang, et al., "Versatile small-molecule motifs for self-assembly in water and the formation of biofunctional supramolecular hydrogels", Langmuir, 27(2):529-37 (2011).
Zidan, et al., "Maximized Mucoadhesion and Skin Permeation of Anti-AIDS-Loaded Niosomal Gels", Pharmaceutics, Drug Delivery and Pharmaceutical Technology, 103:952-964 (2014).

\* cited by examiner

Tenofovir

Tenofovir disoproxil (TDP)

Tenofovir alafenamide (TAF)

US 11,020,410 B2

SELF-ASSEMBLED GELS FORMED WITH ANTI-RETROVIRAL DRUGS, PRODRUGS THEREOF, AND PHARMACEUTICAL USES THEREOF

CROSS-REFERENCE TO RELATED APPLICATIONS

This application is a National Phase application under 35 U.S.C. 371 of PCT/US2018/016835, filed on Feb. 5, 2018, which claims benefit of and priority to U.S. Provisional Application No. 62/454,212, filed on Feb. 3, 2017, which are hereby incorporated herein by reference in their entirety.

STATEMENT REGARDING FEDERALLY SPONSORED RESEARCH OR DEVELOPMENT

This invention was not made with government support.

FIELD OF THE INVENTION

The disclosed technology is generally in the field of controlled delivery of drug, and more particularly, relates to responsive delivery of anti-retrovirals and prodrugs thereof from self-assembled gels.

BACKGROUND OF THE INVENTION

Controlled release of many therapeutic agents can be achieved only with oral formulations or through the use of implantable pumps. This typically is effective only for systemic, not local or targeted, delivery. Oral formulations typically cannot provide delivery for more than 24 hours. Local and/or targeted delivery allows for a higher concentration of therapeutic to be administered without the risk of side effects present at high concentrations. Formulations providing controlled prolonged release can be used to provide more stable pharmacokinetic levels, increased patient compliance, and reduce the number of times drug must be administered.

Self-assembling gels which are stable in vivo for prolonged and/or "smart" drug delivery are described in US2017/0000888. Self-assembly refers to the formation of molecularly defined, higher-ordered structures largely relying on non-covalent interactions. Structures formed from self-assembly are capable of entrapping molecules in solution during the assembly process, resulting in injectable or topical carriers suitable for delivery of hydrophobic and hydrophilic agents. It is difficult to encapsulate very water insoluble or hydrophobic drugs in hydrogels.

Therefore, it is an object of the present invention to provide a self-assembled gels, and processes for making thereof, which can be used for delivery of hydrophobic or water insoluble drugs such as anti-retroviral drugs.

It is another object of the present invention to provide self-assembled gels for prolonged delivery of anti-retroviral drugs in methods of treating patients in need thereof.

SUMMARY OF THE INVENTION

Hydrogel or organogel formulations have been prepared incorporating anti-retroviral drugs. The formulations provide controlled release of the drug after administration. Release can be regulated through the presence of enzymes elevated as a function of disease severity, through the use of enzyme cleavable linkages between the drug and gelator self-assembling to form the gels. The formulations can be provided in the form of gels, lyophilized for administration in dried form which re-hydrates at the site of administration or which is hydrated for administration, disrupted into particles or dispersions, or co-administered with one or mother additional therapeutic, prophylactic or diagnostic agents. In some cases, drug or drug prodrug/gelator may be initially dissolved in a small quantity of a solvent such as dimethylsulfoxide (DMSO) or another GRAS organic solvent, then resuspended in or diluted into an aqueous solution. The gel will typically be filtered, centrifuged, dried or washed to remove the initial solvent so that only a small residue is present in the final formulation.

Examples demonstrate formation of tenofovir and tenofovir derivative gels.

DETAILED DESCRIPTION OF THE INVENTION

I. Definitions

Figure 1:
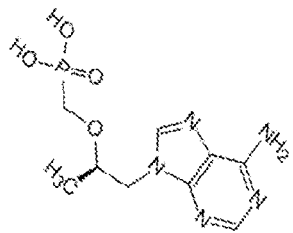
FIG. 1 shows the chemical structures of three different tenofovir anti-retroviral variants.
Figure 1:
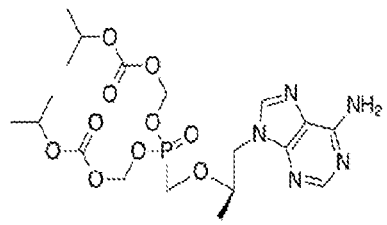
Figure 1:
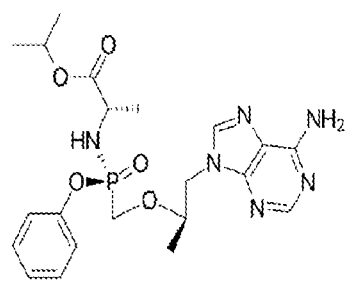

The term "gelators" refer to molecules that can self-assemble through non-covalent interactions, such as hydrogen-bonding, van der Waals interactions, hydrophobic interactions, ionic interactions, pi-pi stacking, or combinations thereof, in one or more solvents. The gelators can form a gel by rigidifying the solvent through, for example, capillary forces. Gelators can include hydrogelators (e.g., gelators that form hydrogels) and organo-gelators (e.g., gelators that form organo-gels). In some embodiments, gelators can form both hydrogels and organo-gels.

The term "co-gelator" refers to a molecule that can be a non-gelator or a gelator and can become integrated within self-assembled structures in at least a partially organized manner, where a non-gelator is not capable of self-assembly on its own and a gelator is capable of self-assembly.

The term "self-assembling" refers to the capability of molecules to spontaneously assemble, or organize, to form a higher ordered structure such as hydrogel or organo-gel in a suitable environment.

The term "hydrogel" refers to three-dimensional (3-D) networks of molecules covalently (e.g., polymeric hydrogels) or non-covalently (e.g., self-assembled hydrogels) held together where water is the major component. Gels can be formed via self-assembly of gelators or via chemical cross-linking of gelators.

The term "organogel" refers to 3-D networks of molecules covalently (e.g., polymeric organogels) or non-covalently (e.g., self-assembled organogels) held together where an organic solvent is the major component. Gels can be formed via self-assembly of gelators or via chemical cross-linking of gelators.

The term "co-assembly", refers to the process of spontaneous assembly, or organization of at least two different types of molecules to form a high ordered structure such as hydrogel or organo-gel in a suitable environment, where molecules in the structure are generally organized in an ordered manner.

The term "organic solvent" refers to any carbon-containing substance that, in its liquid phase, is capable of dissolving a solid substance. Exemplary organic solvents commonly used in organic chemistry include toluene, tetrahydrofuran, acetone, dichloromethane, and hexane.

The term "water-miscible" refers to a solvent that mixes with water, in all proportions, to form a single homogenous liquid phase. This includes solvents like dimethyl sulfoxide (DMSO), tetrahydrofuran, acetone, ethanol, methanol, and dioxane, but generally excludes solvents such as hexane, oils, and ether. It also excludes solvents that have some, very limited miscibility or solubility in water such as ethyl acetate and dichloromethane, which are practically considered immiscible.

The term "percent (%) encapsulated" or "encapsulation percentage" is generally calculated as % encapsulated=weight of encapsulated drug divided by weight of total of initial drug (encapsulated+unencapsulated)×100%.

The term "encapsulation efficiency (EE)" is generally calculated as EE (%)=experimental/measured drug loading divided by the theoretical drug loading×100%.

Gel weight percent (w/v): Total mass of gelator(s) as a percentage of total solvent volume (i.e, organic solvent(s)+water for hydrogels; organic solvents for organogels).

Drug loading efficiency (w/w): Mass of drug as a percentage of total mass of gelator (amphiphile) and co-gelator, if present.

The term "pharmaceutically acceptable," as used herein, refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

The terms "biocompatible" and "biologically compatible," as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

The term "hydrophilic," as used herein, refers to the property of having affinity for water. For example, hydrophilic chemical compounds are primarily soluble in aqueous solutions and/or have a tendency to absorb water. In general, the more hydrophilic a chemical compound is, the more that compound tends to dissolve in, mix with, or be wetted by water.

The term "hydrophobic," as used herein, refers to the property of lacking affinity for or repelling water. For example, the more hydrophobic chemical compounds, the more that the hydrophobic compound tends to not dissolve in, not mix with, or not be wetted by water.

The term "water insoluble drug," refers to drugs whose aqueous solubility is less than 100 µg/mL. The term "low solubility drug," refers to drugs whose aqueous solubility is less than 10 mg/mL.

The term "anti-retroviral drug," refers to drugs which inhibit the reproduction of retroviruses (such as human immunodeficiency virus). Exemplary anti-retrovirals include, but are not limited to nucleoside analogs, or nucleoside reverse transcriptase inhibitors (NRTIs), as discussed in more detail below.

The term "therapeutic agent" refers to an agent that can be administered to prevent or treat one or more symptoms of a disease or disorder. Therapeutic agents can be nucleic acids or analogs thereof, a small molecule (molecular weight of less than 2000 Daltons, more typically less than 1000 Daltons), peptidomimetic, protein, or peptide, carbohydrate or sugar, lipid, or a combination thereof. In some embodiments, cells or cellular materials may be used as therapeutic agents.

The term "treating" or "preventing" a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

The term "therapeutically effective amount" refers to an amount of the therapeutic agent that, when incorporated into and/or onto the self-assembled gel composition, produces some desired effect at a reasonable benefit/risk ratio applicable to any treatment. The effective amount may vary depending on such factors as the disease or condition being treated, the particular formulation being administered, the size of the subject, or the severity of the disease or condition.

The terms "incorporated" refers to incorporating, formulating, or otherwise including an agent into and/or onto a composition, regardless of the manner by which the agent or other material is incorporated.

A "derivative" of a parent compound is a compound that possesses the same core as the parent compound, but differs from the parent compound in bond order, the absence or presence of one or more atoms and/or groups of atoms, or a combination thereof. The derivative can differ from the parent compound, for example, in one or more substituents present on the core, which may include one or more atoms, functional groups, or substructures. In general, a derivative can be formed, at least theoretically, from the parent compound via chemical and/or physical processes.

A carboxylic acid is the group —COOH. Unless specified otherwise the term carboxylic acid embraces both the free acid and carboxylate salt.

An alkyl is the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. In some embodiments, the chain has 1-6 carbons. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" refers to an alkyl group having from one to ten carbons, more preferably from one to six carbon atoms, in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Examples include oxygen, nitrogen, sulfur, and combinations thereof. In certain embodiments, the alkyl group contains between one and four heteroatoms.

Alkenyl and alkynyl refer to unsaturated aliphatic groups containing one or more double or triple bonds analogous in length (e.g., $C_2$-$C_{30}$) and possible substitution to the alkyl groups described above.

Aryl refers to 5-, 6- and 7-membered aromatic rings. The ring may be a carbocyclic, heterocyclic, fused carbocyclic, fused heterocyclic, bicarbocyclic, or biheterocyclic ring system, optionally substituted as described above for alkyl. Broadly defined, "Ar", as used herein, includes 5-, 6- and 7-membered single-ring aromatic groups that may include from zero to four heteroatoms. Examples include, but are not limited to, benzene, pyrrole, furan, thiophene, imidazole, oxazole, thiazole, triazole, pyrazole, pyridine, pyrazine, pyridazine, and pyrimidine. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic.

Alkylaryl refers to an alkyl group substituted with an aryl group (e.g., an aromatic or hetero aromatic group).

Heterocycle or heterocyclic refers to a cyclic radical attached via a ring carbon or nitrogen of a monocyclic or bicyclic ring containing 3-10 ring atoms, and preferably from 5-6 ring atoms, containing carbon and one to four heteroatoms each selected from non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

Heteroaryl refers to a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_8$) alkyl, phenyl, or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

Halogen refers to fluorine, chlorine, bromine, or iodine.

The term "substituted" refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms, such as nitrogen, may have hydrogen substituents and/or any permissible substituents of organic compounds described herein that satisfy the valences of the heteroatoms. "Substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

"Pharmaceutically acceptable salt", as used herein, refers to derivatives of the anti-retroviral compounds (or prodrugs thereof) described herein where the parent compound is modified by making acid or base salts thereof. Example of pharmaceutically acceptable salts include but are not limited to mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, naphthalenesulfonic, methanesulfonic, ethane disulfonic, oxalic, and isethionic salts.

The pharmaceutically acceptable salts of the anti-retroviral compounds (or prodrugs thereof) can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

Numerical ranges disclosed herein disclose individually each possible number in such range, as well as any sub-ranges and combinations of sub-ranges encompassed therein. For example, a carbon range (i.e., $C_1$-$C_{10}$) is intended to disclose individually every possible carbon value and/or sub-range encompassed within. For example, a carbon length range of $C_1$-$C_{10}$ discloses $C_1$, $C_2$, $C_3$, $C_4$, $C_5$, $C_6$, $C_7$, $C_8$, $C_9$, and $C_{10}$, as well as discloses sub-ranges encompassed within, such as $C_2$-$C_9$, $C_3$-$C_8$, $C_1$-$C_5$, etc. Similarly, an integer value range of 1-10 discloses the individual values of 1, 2, 3, 4, 5, 6, 7, 8, and 10, as well as sub-ranges encompassed within. Further, a concentration range or weight percent range or volume percent range, such as from 1% to 2% by weight of the formulation, discloses the individual values and fractions thereof, such as 1%, 1.1%, 1.2%, 1.32%, 1.48% etc., as well as sub-ranges encompassed within.

"GRAS" is an acronym for the phrase Generally Recognized As Safe. Under sections 201(s) and 409 of the Federal Food, Drug, and Cosmetic Act (the Act), any substance that is intentionally added to food is a food additive, that is subject to premarket review and approval by FDA, unless the substance is generally recognized, among qualified experts, as having been adequately shown to be safe under the conditions of its intended use, or unless the use of the substance is otherwise excepted from the definition of a food additive. Under sections 201(s) and 409 of the Act, and FDA's implementing regulations in 21 CFR 170.3 and 21 CFR 170.30, the use of a food substance may be GRAS either through scientific procedures or, for a substance used in food before 1958, through experience based on common use in food Under 21 CFR 170.30(b), general recognition of safety through scientific procedures requires the same quantity and quality of scientific evidence as is required to obtain approval of the substance as a food additive. General recognition of safety through scientific procedures is based upon the application of generally available and accepted scientific data, information, or methods, which ordinarily are published, as well as the application of scientific principles, and may be corroborated by the application of unpublished scientific data, information, or methods. The database of compounds meeting the requirements defined by 21 CFR is found in Title 21: Food and Drugs, Part 184.

II. Self-Assembled Gel for Delivery of Agents Such as Anti-Retrovirals

A. Gelators

A gelator is an amphiphilic compound. This may be formed by binding a hydrophobic compound to a hydrophilic compound, or a hydrophilic compound to a hydrophobic compound, to form an amphiphilic material. A compound such as a therapeutic agent may be bound to an amphiphilic material to form a gelator for delivery of the agent.

1. GRAS Amphiphiles (Gelators)

Representative GRAS amphiphilic gelators are ascorbyl alkanoate, sorbitan alkanoate, triglycerol monoalkanoate, sucrose alkanoate, glycocholic acid, or any combination thereof.

The alkanoate can include a hydrophobic $C_1$-$C_{22}$ alkyl (e.g., acetyl, ethyl, propyl, butyl, pentyl, caprylyl, capryl, lauryl, myristyl, palmityl, stearyl, arachidyl, or behenyl) bonded via a labile linkage (e.g., an ester, a carbamate, a thioester and an amide linkage) to an ascorbyl, sorbitan, triglycerol, or sucrose molecule. For example, the ascorbyl alkanoate can include ascorbyl palmitate, ascorbyl decanoate, ascorbyl laurate, ascorbyl caprylate, ascorbyl myristate, ascorbyl oleate, or any combination thereof. The sorbitan alkanoate can include sorbitan monostearate, sorbitan decanoate, sorbitan laurate, sorbitan caprylate, sorbitan myristate, sorbitan oleate, or any combination thereof. The triglycerol monoalkanoate can include triglycerol monostearate, triglycerol monopalmitate, triglycerol monodecanoate, triglycerol monolaurate, triglycerol monocaprylate, triglycerol monomyristate, triglycerol monooleate, or any combination thereof. The sucrose alkanoate can include sucrose palmitate, sucrose decanoate, sucrose laurate, sucrose caprylate, sucrose myristate, sucrose oleate, or any combination thereof.

In some embodiments, the GRAS amphiphile gelators include ascorbyl palmitate, triglycerol monostearate, sorbitan monostearate, triglycerol monopalmitate, sucrose palmitate, glycocholic acid, or combinations thereof.

Representative low molecular weight GRAS amphiphile gelators include vitamin precursors such as ascorbyl palmitate (vitamin C precursor), retinyl acetate (vitamin A precursor), and alpha-tocopherol acetate (vitamin E precursor).

In some forms, a GRAS amphiphile gelator is formed by synthetically conjugating one or more saturated or unsaturated hydrocarbon chains having $C_1$ to $C_{30}$ groups with a low molecular weight, generally hydrophilic compound, through esterification or a carbamate, anhydride, and/or amide linkage. The range $C_1$ to $C_{30}$ includes $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$ etc. up to $C_{30}$ as wells as ranges falling within $C_1$ to $C_{30}$, for example, $C_1$ to $C_{29}$, $C_2$ to $C_{30}$, $C_3$ to $C_{28}$, etc.

Typically, a viscous hydrogel which is stable to inversion (e.g., resists flow when inverted) is formed by including greater than 3%, 4%, 5% (wt/vol) or more gelators in a liquid medium. The gels can include, independently, from about 0.01 (e.g., from about 0.05, from about 0.5, from about one, from about two, from about three, from about five, from about 10, or about from 15) to about 40 percent (to about 40, to about 30, to about 20, to about 15, to about 10, to about five, to about three, to about two, to about one, to about 0.5, to about 0.05) of each of the GRAS amphiphile gelators by weight per volume. It is important that the gelators are completely dissolved in solvent prior to self-assembly. This may be achieved by admixing with vortexing in an aqueous solution, or by dissolving in a small amount of organic solvent, then diluting into an aqueous solution. The gelators tend to form nanostructures, fibers, micelles, and other solid forms when they self-assemble. These are usually washed by filtration and/or centrifugation, then the washed nanostructures suspended in aqueous solution to form a stable hydrogel or into an organic solvent to form a stable organogel.

In some embodiments, the self-assembled gel compositions described include an enzyme-cleavable, generally recognized as safe (GRAS) first gelator having a molecular weight of 2500 or less and a non-independent second gelator that is also a GRAS agent. Non-independent gelators do not form self-supporting gel at the concentration that would typically form self-supporting gel if combined with an enzyme-cleavable GRAS gelator. Exemplary non-independent second gelators include alpha tocopherol acetate, retinyl acetate, and retinyl palmitate. The non-independent gelators co-assemble with the GRAS first gelators to form the self-assembled gels.

The gels can include, independently, from about three to a maximum of about 30-40 percent, more preferably about 4% to about 10% by weight gelator per volume of gel.

The gels can also include a co-gelator which can become integrated within self-assembled structures in at least a partially organized manner, although the non-gelator is not capable of self-assembly on its own and a gelator is capable of self-assembly. Examplary co-gelator are described in the examples below. Others include tenofovir alafenamide, phospholipids and sterols, for example, cholesterol.

B. Anti-Retroviral Agents and Prodrugs Thereof (Co-Gelators or Gelators)

An estimated 33 million people are infected with HIV worldwide. In the United States, more than 1.2 million people have HIV infection, and almost 1 in 7 (14%) are unaware of their infection. The estimated incidence of HIV in the United States has remained stable in recent years, at about 50,000 new infections occurring each year. Significant advances in antiretroviral therapy have been made since the introduction of zidovudine (AZT) in 1987.

With the advent of highly active antiretroviral therapy (HAART), HIV-1 infection is now manageable as a chronic disease in patients who have access to medication and who achieve durable virologic suppression. HAART provides effective treatment options for treatment-naive and treatment-experienced patients. Six classes of antiretroviral agents currently exist, as follows:

Nucleoside reverse transcriptase inhibitors (NRTIs)

Non-nucleoside reverse transcriptase inhibitors (NNRTIs)

Protease inhibitors (PIs)

Integrase inhibitors (INSTIs)

Fusion inhibitors (FIs)

Chemokine receptor antagonists (CCRS antagonists)

Each class targets a different step in the viral life cycle as the virus infects a CD4+ T lymphocyte or other target cell. The use of these agents in clinical practice is largely dictated by their ease or complexity of use, side-effect profile, efficacy based on clinical evidence, practice guidelines, and clinician preference.

TABLE 1

Classification and Summary of US FDA-Approved Antiretroviral Agents

| Name | Dosage Form (s) | Adult Dose | Adverse Events |
|---|---|---|---|
| Nucleoside reverse transcriptase Inhibitors (NRTIs) | | | |
| Abacavir (Ziagen)[h] | 300-mg tablet; 20-mg/mL oral solution | 600 mg PO qd or 300 mg PO bid Take without regard to meals | Hypersensitivity reaction (may include fever, rash, nausea, vomiting, diarrhea, malaise, shortness of breath, cough, pharyngitis); patients positive for HLA-B*5701 are at highest risk for hypersensitivity (perform HLA screening before initiating) |
| Didanosine (Videx, Videx EC)[h] | 125-mg, 200-mg, 250-mg, 400-mg delayed-released capsule; 10-mg/mL powder for solution | <60 kg: 250 mg PO qd Take 30 min ac or 2 hr pc Oral solution: Divide daily dose bid | Peripheral neuropathy, pancreatitis, nausea, lactic acidosis |
| Emtricitabine (Emtriva)[h] | 200-mg capsule; 10-mg/mL oral solution | 200 mg PO qd (capsule) or 240 mg (24 mL) oral solution PO qd Take without regard to meals | Minimal toxicity, hyperpigmentation |
| Lamivudine (Epivir)[h] | 150-mg, 300-mg tablet; 10-mg/mL oral solution | 150-mg, 300-mg tablet; 10-mg/mL oral solution | Minimal toxicity, severe acute exacerbation of hepatitis may occur with HBV-coinfection upon discontinuation |
| Stavudine (Zerit)[h] | 15-mg, 20-mg, 30-mg, 40-mg capsule; 1-mg/mL oral solution | >60 kg: 40 mg PO bid <60 kg: 30 mg PO bid Take without regard to meals | Peripheral neuropathy, pancreatitis, lactic acidosis, lipoatrophy, hyperlipidemia |
| Tenofovir DF (Viread)[h] | 300-mg tablet | 300 mg PO qd Take without regard to meals | Nausea, vomiting, diarrhea, headache, asthenia, renal insufficiency |
| Zalcitabine (Hivid) Product discontinued | 0.375-mg, 0.75-mg tablet | 0.75 mg PO tid | Peripheral neuropathy, pancreatitis, lactic acidosis, stomatitis |
| Zidovudine (Retrovir)[h] | 300-mg tablet; 100-mg capsule; 10-mg/mL oral solution; 10-mg/mL intravenous solution | 300 mg PO bid or 200 mg PO tid Take without regard to meals | Nausea, vomiting, headache, asthenia, anemia, neutropenia |
| Non-nucleoside reverse transcriptase inhibitors (NNRTIs) | | | |
| Delavirdine (Rescriptor) Note: Discontinued in the U.S. with estimated availability for 100-mg tablets until October 2018 and for 200-mg tablets until February 2020 | 100-mg, 200-mg tablets | 400 mg PO tid | Rash, headache |
| Efavirenz (Sustiva) | 600-mg tablet; 50-mg, 200-mg capsule | 600 mg PO qd Take on empty stomach to decrease adverse effects | Rash, CNS (eg, somnolence, vivid dreams, confusion, visual hallucinations), hyperlipidemia |
| Etravirine (Intelence)[d] | 25-mg, 100-mg, 200-mg tablets | 200 mg PO bid following a meal | Rash, nausea |
| Nevirapine (Viramune, Viramune XR) | 200-mg tablet; 400 mg XR tablet; 10-mg/mL suspension | 200 mg PO bid[a] XR: 400 mg PO qd Take without regard to meals | Rash, hepatitis |
| Rilpivirine (Edurant) | 25-mg tablet | 25 mg PO qd with a meal | Depressive disorders, insomnia, headache, rash |
| Protease inhibitors (PIs) | | | |
| Atazanavir (Reyataz) | 100-mg, 150-mg, 200-mg, 300-mg capsules 50-mg single packet oral powder | 400 mg PO qd or 300 mg + ritonavir 100 mg PO qd Take with food | Indirect hyperbilirubinemia, prolonged PR interval, hyperglycemia, skin rash (20%), hyperlipidemia |
| Darunavir (Prezista) | 75-mg, 150-mg, 300-mg, 400-mg, 600-mg tablets | 800 mg qd + ritonavir 100 mg PO qd[b] or 600 mg bid + ritonavir 100 mg PO bid Take with food | Rash, nausea, diarrhea, hyperlipidemia, hyperglycemia |
| Fosamprenavir (Lexiva) | 700-mg tablet; 50-mg/mL oral suspension | 700 mg bid + ritonavir 100 mg PO bid or 1400 mg PO bid or 1400 mg + ritonavir 100-200 mg PO qd[b] Suspension: Take without food | Rash, nausea, vomiting, diarrhea, hyperlipidemia, hyperglycemia |

TABLE 1-continued

Classification and Summary of US FDA-Approved Antiretroviral Agents

| Name | Dosage Form (s) | Adult Dose | Adverse Events |
| --- | --- | --- | --- |
| Indinavir (Crixivan) | 100-mg, 200-mg, 400-mg capsules | Boosted with RTV: Take with food<br>800 mg PO q8h Take 1 h ac or 2 h pc; may take with skim milk or low-fat meal<br>800 mg PO bid + ritonavir 100-200 mg PO bid without regard for meals | Nephrolithiasis, nausea, indirect hyperbilirubinemia, hyperlipidemia, hyperglycemia |
| Lopinavir/ritonavir (Kaletra) | 100-mg/25-mg, 200-mg/50-mg tablets; 80-mg/20-mg per mL oral solution | 400 mg/100 mg PO bid or 800 mg/200 mg PO qd[b]<br>Tablet: Take without regard to meals | Nausea, vomiting, diarrhea, asthenia, hyperlipidemia, hyperglycemia |
| Nelfinavir (Viracept) | 250-mg, 625-mg tablets, 50 mg/g oral powder | 750 mg PO tid (Nelfinavir cannot be boosted)<br>Take with food | Diarrhea, hyperlipidemia, hyperglycemia |
| Ritonavir (Norvir) | 100-mg tablet; 100-mg soft gelatin capsule; 80-mg/mL oral solution | Nonboosting dose (Ritonavir used as sole protease inhibitor): 600 mg bid[c]<br>Tablet: Take with food | Nausea, vomiting, diarrhea, asthenia, hyperlipidemia, oral paresthesias, hyperglycemia |
| Saquinavir (Invirase) | 500-mg tablet; 200-mg hard gelatin capsule | 1000 mg + ritonavir 100 mg PO bid<br>Unboosted saquinavir is not recommended<br>Take with food, or within 2 h pc | Nausea, diarrhea, headache, hyperlipidemia, hyperglycemia, PR and QT interval prolongation |
| Tipranavir (Aptivus)[d] | 250-mg soft gelatin capsule<br>100-mg/mL oral solution | 500 mg + ritonavir 200 mg PO bid without regard to meals<br>Unboosted tipranavir is not recommended | Hepatotoxicity, rash, hyperlipidemia, hyperglycemia, intracranial hemorrhage (rare cases reported) |
| Integrase inhibitors (II) | | | |
| Raltegravir (Isentress, Isentress HD) | 400-mg tablet<br>600-mg tablet | Isentress with rifampin: 800 mg PO bid<br>Isentress HD: 1200 mg PO once daily (for use in treatment-naive or virologically suppressed on an initial regimen of 400 mg bid)<br>Take without regard to meals | Nausea, diarrhea, headache, CK elevations, myopathy/rhabdomyolysis (rare) |
| Dolutegravir (Tivicay) | 50-mg tablet | 50 mg PO once daily<br>With UGT1A/CY3A inducers (eg, efavirenz, fosamprenavir/ritonavir, tipranavir/ritonavir, rifampin): 50 mg PO BID<br>Take without regard to meals | Cholesterol and TG elevations, CK elevations, liver enzyme elevations, hyperglycemia |
| Elvitegravir (Vitekta)[f] | 85-mg, 150-mg tablet | 85 mg PO once daily plus atazanavir or lopinavir plus ritonavir or 150 mg PO once daily plus darunavir or fosamprenavir or tipranavir plus ritonavir<br>Take with food | Immune reconstitution syndrome |
| Chemokine receptor antagonist (CCR5 antagonist) | | | |
| Maraviroc (Selzentry) | 150-mg, 300-mg tablets | 150 mg PO bid (CYP3A4 inhibitors ± inducers)<br>600 mg PO bid (CYP3A4 inducers)<br>Take without regard to meals | Constipation, dizziness, infection, rash |
| Fusion inhibitor (FI) | | | |
| Enfuvirtide (Fuzeon)[d] | 90-mg/mL powder for injection | 90 mg SC bid | Injection-site reactions (eg, pain, erythema, induration, nodules) |

TABLE 1-continued

Classification and Summary of US FDA-Approved Antiretroviral Agents

| Name | Dosage Form (s) | Adult Dose | Adverse Events |
|---|---|---|---|
| Combination formulations | | | |
| Stribild - elvitegravir (150 mg) + cobicistat[e] (150 mg) | +emtricitabine (200 mg) +tenofovir DF (300 mg) | Qd: this is a complete once-daily regimen | |
| Genvoya - elvitegravir (150 mg) + cobicistat (150 mg) | +emtricitabine (200 mg) +tenofovir AF[g] (10 mg) | qd; this is a complete once-daily regimen | |
| Odefsey - emtricitabine (200 mg) | +rilpivirine (25 mg) + tenofovir AF (25 mg) | qd; this is a complete once-daily regimen | |
| Complera - emtricitabine (200 mg) | +rilpivirine (25 mg) + tenofovir DF (300 mg) | qd; this is a complete once-daily regimen | |
| Juluca - dolutegravir (50 mg) + rilpivirine (25 mg) | | | qd; this is a complete once-daily regimen in adults who are virologically suppressed (HIV-1 RNA <50 copies/mL) on a stable ART regimen for ≥6 months with no history of treatment failure and no known substitutions associated with resistance |
| Descovy - emtricitabine (200 mg) + tenofovir AF (25 mg) qd | | | |
| Truvada - emtricitabine (200 mg) | +tenofovir DF (300 mg) qd | | |
| Epzicom - abacavir (600 mg) | +lamivudine (300 mg) qd | | |
| Triumeq - abacavir (300 mg) + dolutegravir (50 mg) | +lamivudine (300 mg) qd | | |
| Trizivir - abacavir (300 mg) | +lamivudine (150 mg) + zidovudine (300 mg) bid | | |
| Atripla - tenofovir DF (300 mg) | +emtricitabine (200 mg) +efavirenz (600 mg) qd | | |
| Combivir - zidovudine (300 mg) | +lamivudine (150 mg) bid | | |
| Evotaz - atazanavir (300 mg) | +cobicistat (150 mg) qd | | |
| Prezcobix - darunavir ethanolate (800 mg) | +cobicistat (150 mg) qd | | |

In some embodiments, the gelators are anti-retrovirals and prodrugs of such anti-retrovirals which are used in formation of the gels described herein.

In one non-limiting embodiment, a method of making an anti-retroviral prodrug can be carried out as follows. The anti-retroviral prodrugs can be synthesized by the covalent attachment of one or more hydrophobic moieties which include, but are not limited to primary alcohols, including diols to the active agent (the anti-retroviral drug molecule). In some other embodiments, the hydrophobic moieties can include, but are not limited to haloalkanes (such as chloro- or bromo-alkyls having chains of between 4-18 carbons in length) to the active agent (the anti-retroviral drug molecule).

In one non-limiting example, the hydrophobic moiety, such as a primary alcohol or diol, can be conjugated to a drug (anti-retroviral) molecule as follows. To an oven dried suitable container (such as a flask) is added 1.0 equivalents of the anti-retroviral, 1.05 equivalents of Carbodiimide coupling reagent (typically N,N'-dicyclohexylcarbodiimide or N,N'-diisopropylcarbodiimide), 0.1 equivalents of 4-dimethylaminopyridine, up to 5 equivalents of a primary alcohol (including, but not limited to, saturated primary alcohol alkyl chains between 4-18 carbons in length and diols thereof). It is believed that chain length of the hydrophobic moiety can be used to control the release kinetics of the anti-retroviral drug attached thereto. For example, use of short cleavable alkyl chain lengths (less than six carbons) may demonstrate prolonged drug release, use of long cleavable alkyl chain lengths (more than 12 carbons) may demonstrate slow release in comparison to short alkyl chain lengths, and intermediate alkyl chain lengths (six to twelve carbons) may demonstrate release kinetics which are in between. The material is suspended in an organic nitrogenous base (such as, but not limited to, dry pyridine, dimethylformamide, N-methyl-2-pyrrolidone or triethylamine) which may be dried over molecular sieves. This suspension is heated (to about 50-150° C., preferably at least about 100° C.) and stirred for between about 5-72 hours and then cooled to room temperature. To the reaction mixture is added to a mixture of an organic solvent in a suitable amount (such as 75 mL of chloroform) and an alkaline aqueous wash (such as 75 mL 1 mM NaOH (aq)). The aqueous layer is isolated and an aqueous acidic solution (such as 12M HCl (aq)) is added dropwise until pH<2. The material is washed with 5% HCl (aq), filtered and the filtrate is dried under reduced pressure to afford the desired prodrug. Column chromatography on silica gel can be performed for purification, using, for example, a gradient of methanol in chloroform. Yields are generally between 20 and 75%, depending on the exact anti-retroviral prodrug being synthesized.

Another non-limiting exemplary method is as follows. To an oven dried suitable container (such as a flask) is added a $C_4$-$C_{15}$ alkyl primary alcohol (1 eq.) which is stirred in a suitable solvent (such as diethyl ether) at 0° C. under an inert atmosphere (such as of nitrogen or argon). Then is added chloromethyl chloroformate (1.1 eq.) dropwise followed by the addition of an organic nitrogenous base (such as, but not limited to, dry pyridine, dimethylformamide, N-methyl-2-pyrrolidone or triethylamine) which is pyridine (3 eq.). The reaction is warmed to room temperature and stirred for a suitable amount of time, such as 3-6 hours. The organic layer was washed with 1M HCl (aq) twice, brine, and is concentrated under reduced pressure. The resulting material was dissolved in ethyl acetate and column chromatography was performed using a gradient of ethyl acetate in hexanes to afford the product as a white solid. The resulting chloromethyl alkyl carbonate (1 eq.) is dissolved in acetone and potassium iodide (10 eq.) is added and stirred at room temperature for 3-5 days. The reaction mixture was concentrated under reduced pressure, dissolved in diethyl ether and the organic layer is washed with water twice and brine. The organic layer was dried with sodium sulfate and is concentrated under reduced pressure to afford the product in yields typically between 30-75%. The resulting iodomethyl alkyl carbonate (1.1 eq) is dissolved in dimethylformamide and a prodrug molecule, such as tenofovir, (1 eq.) are added diisopropylethylamine (3 eq.) and stirred vigorously for 24 hours at 50° C. The DMF was removed under reduced pressure, the material is dissolved in chloroform and is purified via silica gel column chromatography using a gradient of methanol in chloroform.

In yet another non-limiting example, the hydrophobic moiety, such as a haloalkane (halogen-containing alkyl chains of between 4-18 carbons in length), can be conjugated to a drug (anti-retroviral) molecule as follows. It is believed that chain length of the hydrophobic moiety can be used to control the release kinetics of the anti-retroviral drug attached thereto. For example, use of short cleavable alkyl chain lengths may demonstrate prolonged drug release, use of long cleavable alkyl chain lengths may demonstrate slow release in comparison to short alkyl chain lengths, and intermediate alkyl chain lengths may demonstrate release kinetics which are in between (i.e., alkyl chain lengths (more than 12 carbons) may demonstrate slow release in comparison to short alkyl chain lengths, and intermediate alkyl chain lengths (six to twelve carbons) may demonstrate release kinetics which are in between). In one example, an equivalent of the anti-retroviral drug is added to an oven dried suitable container (such as a flask or scintillation vial). 1.3 equivalents of a haloalkane (such as, but not limited to, 1-iodooctadecane) is then added to the same container with 3 equivalents of base, such as triethylamine (TEA). An organic solvent, such as dimethylformamide (DMF) is added to the container. The container is placed under an inert atmosphere, such as nitrogen or argon atmosphere. The container is heated (to a temperature in between about 50 to about 100° C., more preferably about 80° C.) and allowed to stir (for at least about 5 to about 24 hours, preferably at least about 18 hours). Afterward, the container is allowed to cool to room temperature and the reaction mixture is separated via chromatography. Product fractions can be collected and concentrated under reduced pressure to recover the desired prodrug compound.

In some embodiments, the hydrophobic moieties described above and which are conjugated to a drug (anti-retroviral) molecule are conjugated to the molecule through a cleavable linker, such as an enzymatically cleavable linker as described in further detail below. Additionally, it is known that the hydrophobicity of drugs, such as tenofovir and related derivatives shown in FIG. 1, affect the physico-chemical properties such as potency (i.e., HIV-1 activity ($IC_{50}$ μM)) where increasing hydrophobicity results in increasing potency. Accordingly, it is believed that the controlling the degree of hydrophobicity of the hydrophobic moieties coupled to the drugs also permits control of the potency of the anti-retroviral prodrugs described herein.

A person of ordinary skill in the art would appreciate that the conditions disclosed in the above methods of synthesizing prodrugs are non-limiting examples and that other synthetic methods may also be used or devised to achieve the desired prodrugs, such as of Formulae (I) or (III) below. The person of skill in the art would also be able to adjust the synthesis conditions (i.e., solvent selection, temperatures, etc.), workup, and purification procedures to obtain desired target prodrugs according to the general procedures described herein depending on the exact anti-retroviral prodrug which is being synthesized.

In preferred embodiments, the anti-retrovirals (co-gelators) may be tenofovir and derivatives thereof, tenofovir alafenamide, cabotegravir, rilpivirine, emtricitabine, abacavir, lamivudine, adefovir, or derivatives of any of those listed herein. In some embodiments, the one or more anti-retrovirals may be pharmaceutically acceptable salts of anti-retrovirals of tenofovir and derivatives thereof, tenofovir alafenamide, cabotegravir, rilpivirine, emtricitabine, abacavir, lamivudine, adefovir, or other known anti-retrovirals which are commercially available, or derivatives of any of those listed herein. Methods of preparing pharmaceutically acceptable salts of anti-retroviral drugs are known. In some embodiments, the anti-retroviral is a fumarate salt of tenofovir alafenamide In one embodiment, the anti-retroviral is tenofovir or derivatives thereof, as shown in FIG. 1.

In some embodiments, the anti-retroviral prodrug is defined according Formula (I):

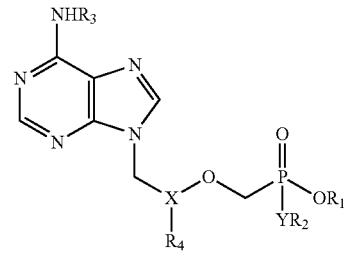

Formula (I)

or a pharmaceutically acceptable salt, hydrate, solvate or stereoisomer thereof, wherein $R_1$ is H, alkyl, heteroalkyl, aryl, heteroaryl, —CH((CH$_2$)$_n$CH$_3$)C(O)O-alkyl, —(CH$_2$)$_n$OC(O)O-alkyl;

$R_2$ is H, alkyl, heteroalkyl, aryl, heteroaryl, —CH((CH$_2$)$_n$CH$_3$)C(O)O-alkyl, —(CH$_2$)$_n$OC(O)O-alkyl;

$R_3$ is H or alkyl;

$R_4$ is H or alkyl;

$R_5$ is H or alkyl;

Y is NH or O;

n is an integer from 0 to 10; and wherein each alkyl, heteroalkyl, aryl, heteroaryl may be optionally substituted with one or more of alkyl, halogen, hydroxyl, amine, amide, carboxylic acid, hydroxamide, sulfhydryl or phosphate groups.

An exemplary compound of Formula (I) is defined according to Formula (II) below:

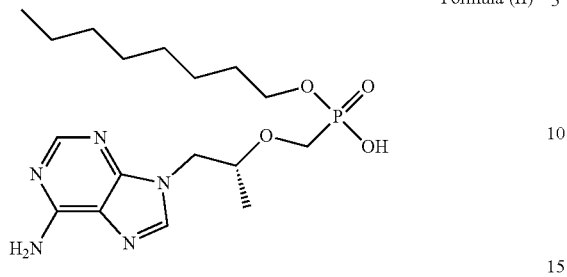

Formula (II)

Additional compounds of Formula (I) include, but are not limited to:

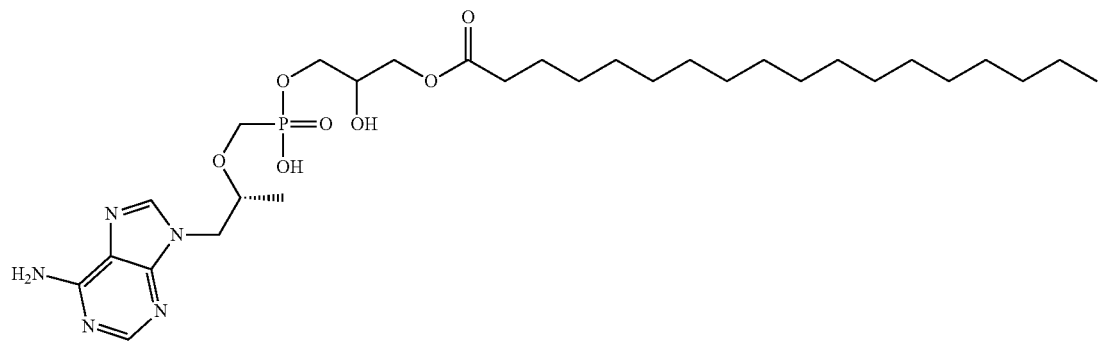

3-((((((R)-1-(6-amino-9H-purin-9-yl) propan-2-yl)oxy)methyl)phosphoryl)oxy)-2-hydroxypropylstearate

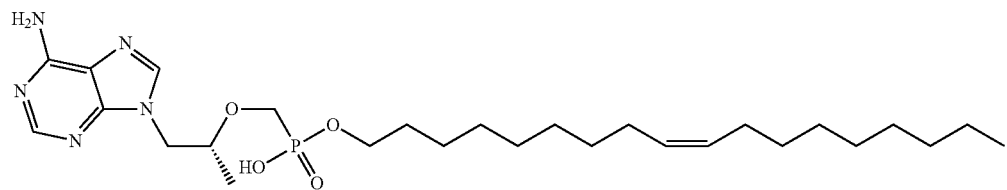

(Z)-octadec-9-en-1-yl hydrogen ((((R)-1-(6-amino-9H-purin-9-yl)propan-2-yl)oxy)methyl)phosphonate

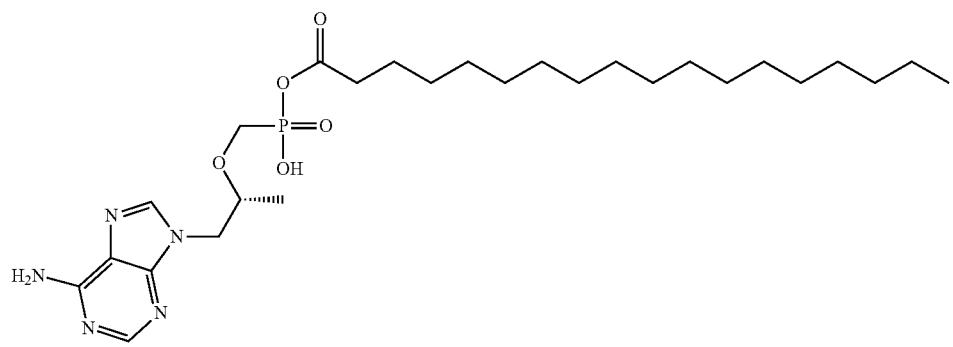

(R)-(((1-(6-amino-9H-purin-9-yl)propan-2-yl)oxy)methyl)phosphonic stearic anhydride -continued

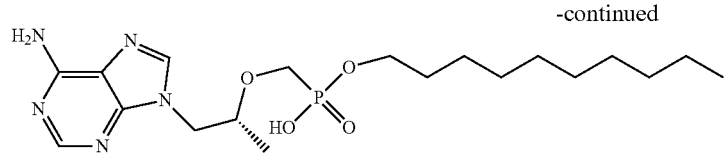

decyl hydrogen ((((R)-1-(6-amino-9H-purin-9-yl)propan-2-yl)oxy)methyl)phosphonate

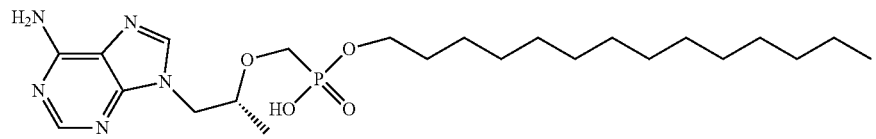

tetradecyl hydrogen ((((R)-1-(6-amino-9H-purin-9-yl)propan-2-yl)oxy)methyl)phosphonate

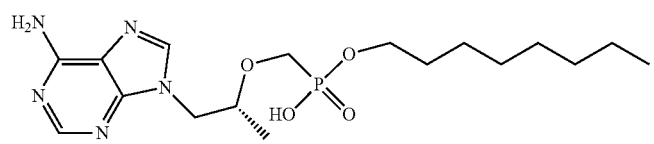

octyl hydrogen ((((R)-1-(6-amino-9H-purin-9-yl)propan-2-yl)oxy)methyl)phosphonate

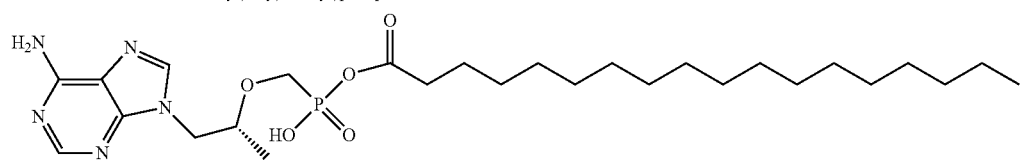

(R)-(((1-(6-amino-9H-purin-9-yl)propan-2-yl)oxy)methyl)phosphonic stearic anhydride

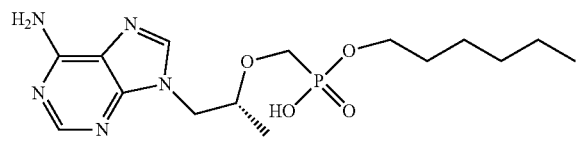

hexyl hydrogen ((((R)-1-(6-amino-9H-purin-9-yl)propan-2-yl)oxy)methyl)phosphonate

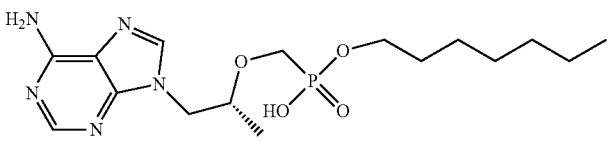

heptyl hydrogen ((((R)-1-(6-amino-9H-purin-9-yl)propan-2-yl)oxy)methyl)phosphonate

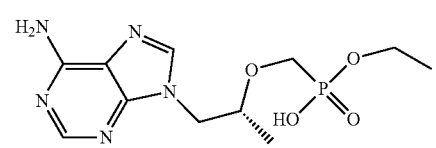

ethyl hydrogen ((((R)-1-(6-amino-9H-purin-9-yl)propan-2-yl)oxy)methyl)phosphonate

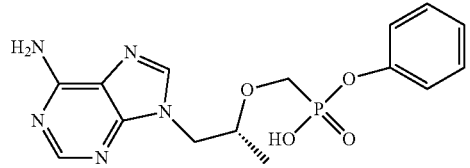

phenyl hydrogen ((((R)-1-(6-amino-9H-purin-9-yl)propan-2-yl)oxy)methyl)phosphonate

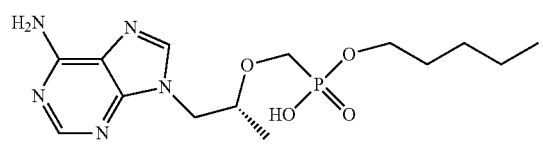

pentyl hydrogen ((((R)-1-(6-amino-9H-purin-9-yl)propan-2-yl)oxy)methyl)phosphonate

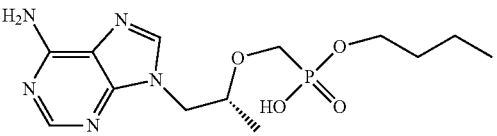

butyl hydrogen ((((R)-1-(6-amino-9H-purin-9-yl)propan-2-yl)oxy)methyl)phosphonate -continued

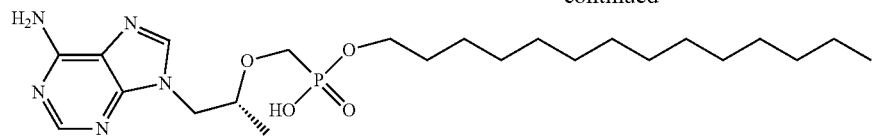

tetradecyl hydrogen ((((R)-1-(6-amino-9H-purin-9-yl)propan-2-yl)oxy)methyl)phosphonate

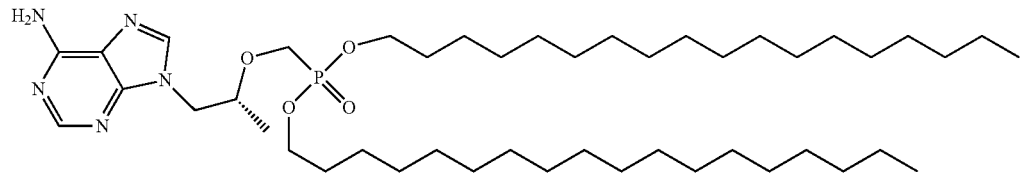

dioctadecyl (R)-(((1-(6-amino-9H-purin-9-yl)propan-2-yl)oxy)methyl)phosphonate

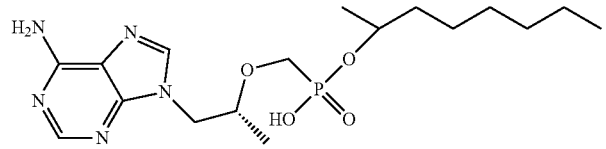

octan-2-yl hydrogen ((((R)-1-(6-amino-9H-purin-9-yl)propan-2-yl)oxy)methyl)phosphonate

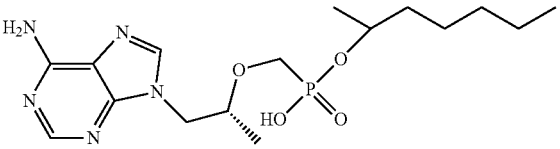

heptan-2-yl hydrogen ((((R)-1-(6-amino-9H-purin-9-yl)propan-2-yl)oxy)methyl)phosphonate

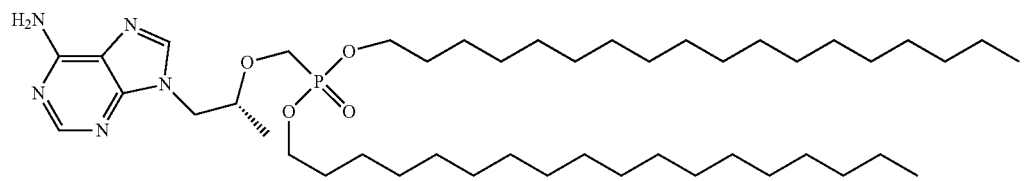

dioctadecyl (R)-(((1-(6-amino-9H-purin-9-yl)propan-2-yl)oxy)methyl)phosphonate

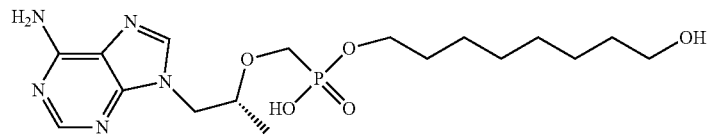

8-hydroxyoctyl hydrogen ((((R)-1-(6-amino-9H-purin-9-yl)propan-2-yl)oxy)methyl)phosphonate

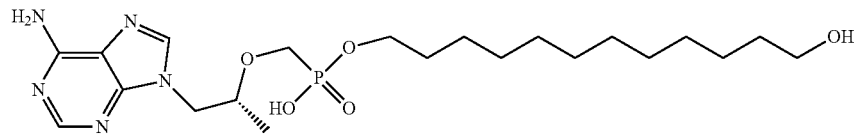

12-hydroxydodecyl hydrogen ((((R)-1-(6-amino-9H-purin-9-yl)propan-2-yl)oxy)methyl)phosphonate

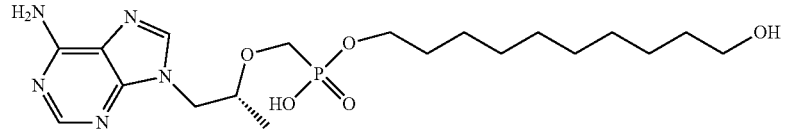

10-hydroxydecyl hydrogen ((((R)-1-(6-amino-9H-purin-9-yl)propan-2-yl)oxy)methyl)phosphonate -continued

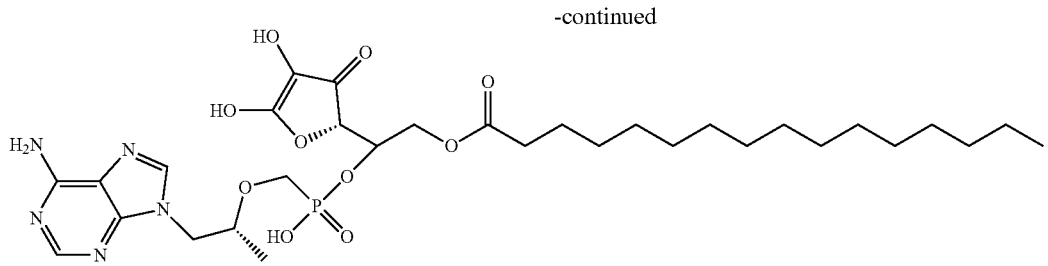

2-((((R)-1-(6-amino-9H-purin-9-yl)propan-2-yl)oxy)methyl)(hydroxy)phosphoryl)oxy)-2-((S)-4,5-dihydroxy-3-oxo-2,3-dihydrofuran-2-yl)ethyl palmitate

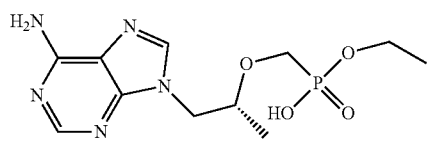

ethyl hydrogen ((((R)-1-(6-amino-9H-purin-9-yl)propan-2-yl)oxy)methyl)phosphonate When a diol is used according to the exemplary synthetic methods described above, the anti-retroviral prodrug produced can be a dimer prodrug defined, for example, according to Formula (III):

Formula (III)

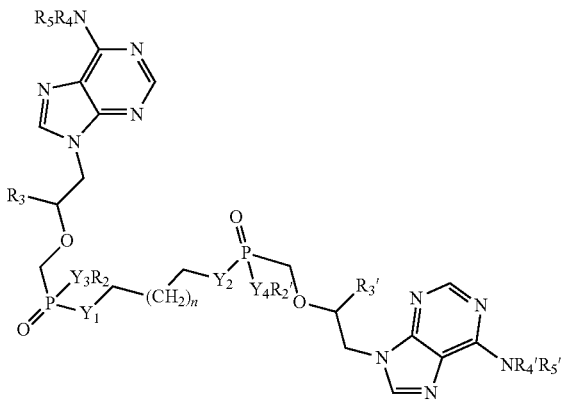

or a pharmaceutically acceptable salt, hydrate, solvate or stereoisomer thereof, wherein $R_2$ and $R_{2'}$ are each independently H, alkyl, heteroalkyl, aryl, heteroaryl, —CH((CH$_2$)$_n$CH$_3$)C(O)O-alkyl, —(CH$_2$)$_n$OC(O)O-alkyl;

$R_3$ and $R_{3'}$ are each independently H or alkyl;

$R_4$ and $R_{4'}$ are each independently H or alkyl;

$R_5$ and $R_{5'}$ are each independently H or alkyl;

$Y_1$, $Y_2$, $Y_3$ and $Y_4$ are each independently NH or O; and n is an integer from 0-10, wherein each alkyl, halogen, heteroalkyl, aryl, heteroaryl may be optionally substituted with one or more of alkyl, hydroxyl, amine, amide, carboxylic acid, hydroxamide, sulfhydryl or phosphate groups.

Exemplary compounds of Formula (III) include, but are not limited to:

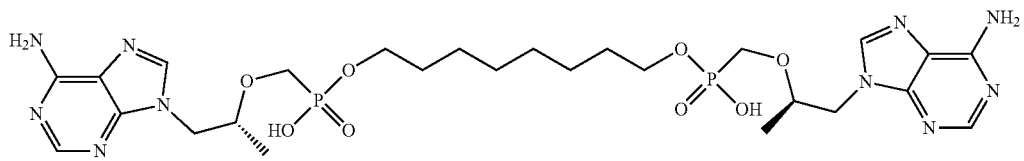

octane-1,8-diyl bis(hydrogen ((((R)-1-(6-amino-9H-purin-9-yl)propan-2-yl)oxy)methyl)phosphonate)

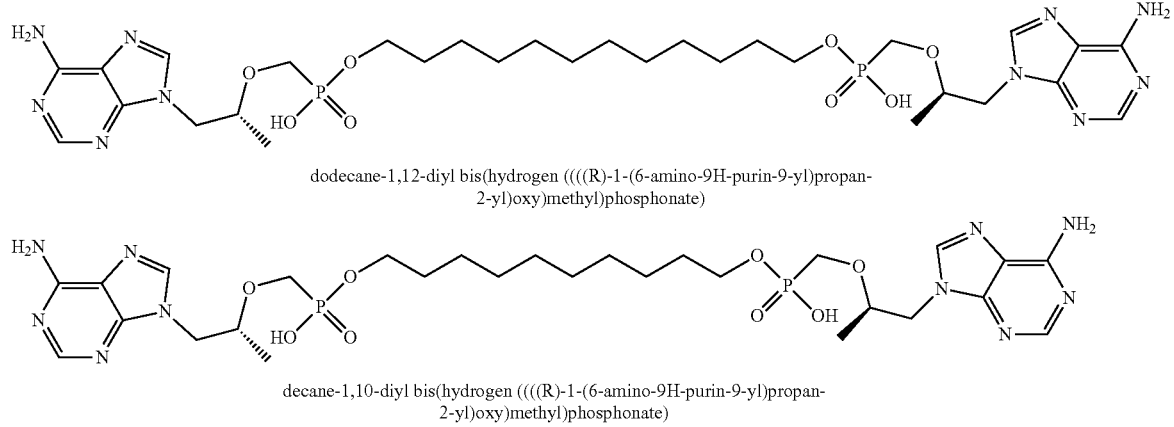

dodecane-1,12-diyl bis(hydrogen ((((R)-1-(6-amino-9H-purin-9-yl)propan-2-yl)oxy)methyl)phosphonate)

decane-1,10-diyl bis(hydrogen ((((R)-1-(6-amino-9H-purin-9-yl)propan-2-yl)oxy)methyl)phosphonate)

The anti-retroviral-based prodrugs described above may be used as a gelator and/or co-gelator. For instance, the prodrugs may be used according to methods of forming gels described herein.

The functional groups of the (co)gelator promote self-assembly by facilitating hydrogen bonding, intermolecular interactions through pi-pi stacking, and molecular association through van der Waals interactions, as discussed above.

The anti-retroviral-based prodrugs described above may have one or more chiral centers and thus exist as one or more stereoisomers. Such stereoisomers can exist as a single enantiomer, a mixture of diastereomers or a racemic mixture are encompassed by the present disclosure. As used herein, the term "stereoisomers" refers to compounds made up of the same atoms having the same bond order but having different three-dimensional arrangements of atoms which are not interchangeable. The three-dimensional structures are called configurations. As used herein, the term "enantiomers" refers to two stereoisomers which are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

C. Optional therapeutic, Prophylactic, and Diagnostic Active Agents

The hydrogel and organogel compositions described above may also contain, in addition to the anti-retrovirals described, one or more additional therapeutic, prophylactic or diagnostic agents. Therapeutic, prophylactic and diagnostic agents may be proteins, anti-inflammatory drugs, steroids, contraceptives, antibiotics, immunosuppressants, chemotherapeutics, sensitizing agents, antibodies, antibody fragments, proteins, peptides, growth factors, cytokines, cells, stem cells, siRNA, vitamins and any combination thereof for their co-delivery with the anti-retroviral drugs.

In other forms, the additional therapeutic, prophylactic, or diagnostic agents may be physically entrapped, encapsulated, or non-covalently associated with the nanostructures in the gel composition. The therapeutic, prophylactic, or diagnostic agents may be covalently modified with one or more gelators, one or more stabilizers, or be used as a gelator itself. Alternatively, they are incorporated into the assembled ordered lamellar, vesicular, and/or nanofibrous structures of the gel composition or positioned on the surface of the assembled structures.

Suitable agents can include immunomodulatory molecules such as steroids, non-antiinflammatory agents, chemotherapeutics, anesthetics, analgesics, anti-pyretic agents, anti-infectious agents such as antibacterial, antifungal agents, vitamins, therapeutic RNAs such as small interfering RNA, microRNA, PiRNA, ribozymes, and nucleotides encoding proteins or peptides, and in some cases, cells.

Exemplary proteins to encapsulate in self-assembled gel include enzymes (e.g., lysozyme), antibodies (e.g., immunoglobulin, monoclonal antibody, and antigen binding fragments thereof), growth factors (e.g., recombinant human growth factors), antigens, and peptides such as insulin.

In some embodiments, the additional agents described herein are encapsulated or loaded in the self-assembled gel and one or more of the agents may potentiate the efficacy of another such as the one or more anti-retroviral drugs. In another embodiment, the self-assembled gel compositions include a mixture of therapeutic agents (e.g., a cocktail of agents) for continuous delivery to a tissue or a cell in need thereof.

Diagnostic agents can be included in the self-assembled gel composition and may include paramagnetic molecules, fluorescent compounds, magnetic molecules, and radionuclides. Suitable diagnostic agents include, but are not limited to, x-ray imaging agents and contrast media. Radionuclides can be used as imaging agents. Examples of other suitable contrast agents include gases or gas emitting compounds, which are radiopaque.

The additional agents described herein are optional but may in general be encapsulated at a concentration between about 1 mg/mL and about 200 mg/mL in the self-assembled gels described.

D. Gel Properties

Mechanical Properties & Injectability

With self-assembled hydrogel or organogel compositions, no gravitational flow is observed upon inversion of a container at room temperature for at least 10 seconds, and in some cases, for about 1 hour, about 3 hours, about 1 day, about 2 days, about 3 days, about one week or longer. A self-assembled gel is homogeneous and stable to inversion, unlike heterogeneous materials that is a mixture of gelled regions (non-flowable) and non-gelled, liquid regions (flowable). A self-assembled gel is also different from liposome or micelle suspensions. Liposome or micelles suspensions are not self-supporting and can flow when the container is inverted.

In some embodiments, the self-assembled gel compositions have recoverable rheological properties, i.e., self-assembled gel is shear-thinning, suitable for injection, and recovers to a self-supporting state after cessation of a shear force. The self-supporting state generally features an elastic modulus of from about 10 to about 10,000 Pascal and greater than a viscous modulus. Due to non-covalent interactions for the assembly of gelators and cationic agents, a bulk gel may deform and be extruded under a shear force (e.g., during injection), and the gelators and cationic agents re-assemble upon cessation of shear forces to a self-supporting, stable-to-inversion state (e.g., elastic modulus G' greater than viscous modulus G").

Alternatively, the self-assembled gel composition is injectable as suspended in a pharmaceutically acceptable carrier, i.e., a suspension medium, being a fibrous suspension state.

Another form of the self-assembled gel is a microparticle or nanoparticle, where the bulk self-supporting gel is homogenized, sonicated, wet milled, or otherwise dispersed in a suspension medium and further collected.

Micro- and/or Nano-Structures

The one or more anti-retrovirals and optional agents described can be encapsulated and/or entrapped within or between the nanostructures, can be non-covalently bonded to the nanostructures, or both.

Figure 2:
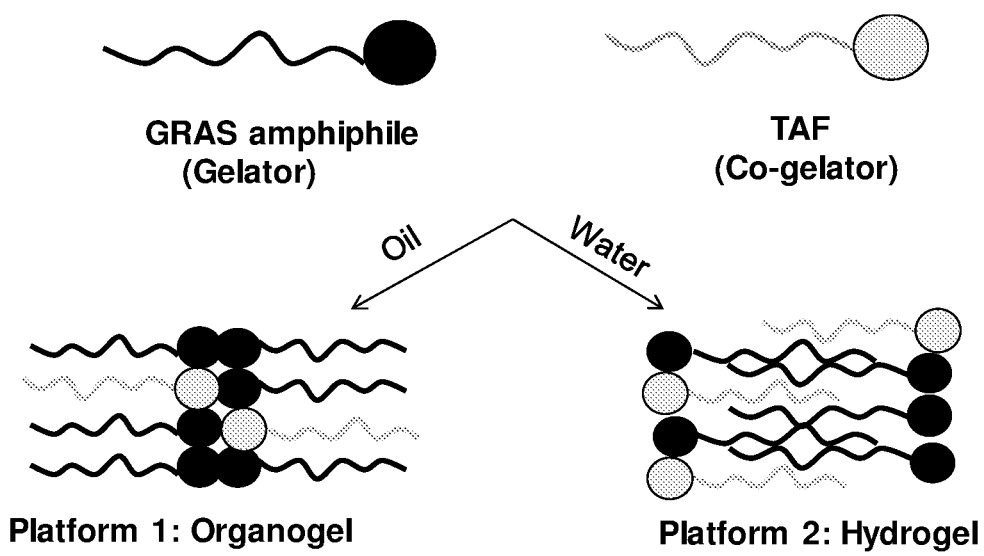
FIG. 2 shows a non-limiting representation of GRAS amphiphile gelator and tenofovir alafenamide (TAF) co-gelator co-assembling into organogel or hydrogel.
Figure 3:
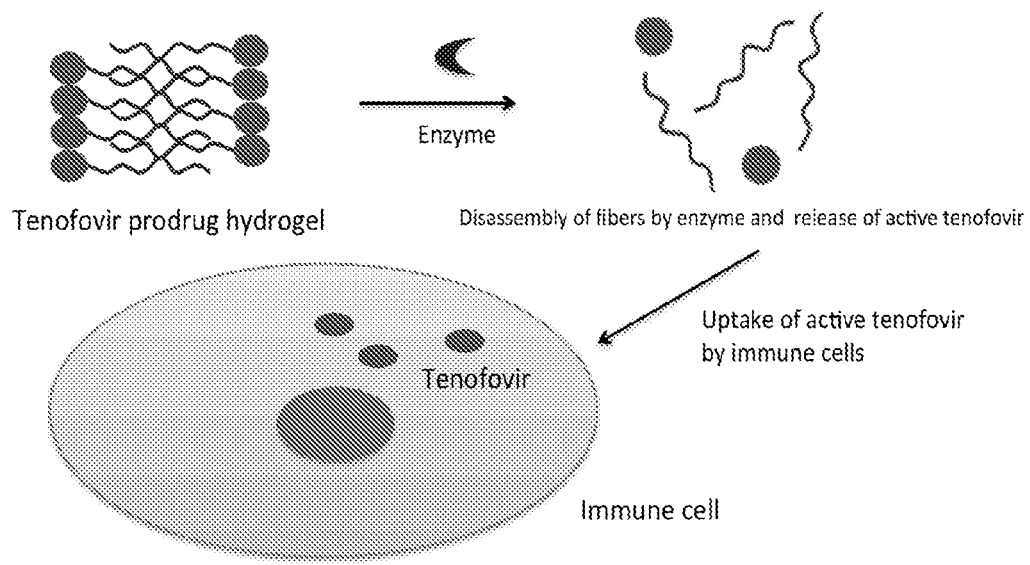
FIG. 3 is a non-limiting scheme of a tenofovir-based prodrug hydrogel which is enzymatically cleavable resulting in disassembly of the gel fibers and release of active tenofovir followed by uptake by immune cells.
Figure 4:
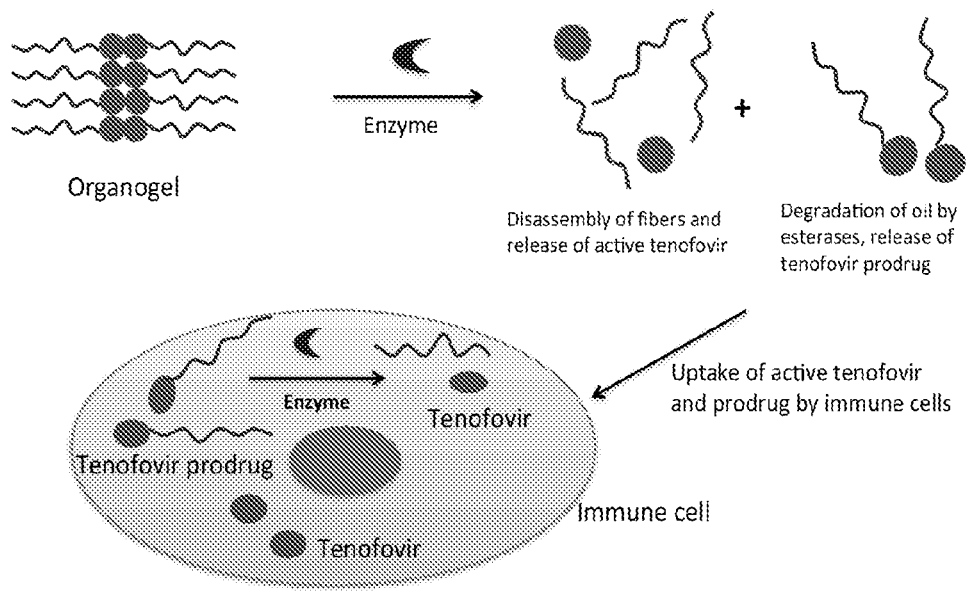
FIG. 4 is a non-limiting scheme of a tenofovir-based prodrug organogel which is enzymatically cleavable resulting in disassembly of the gel fibers, as well as degradation of oil by esterases, and release of tenofovir prodrug which is taken up by immune cells and is enzymatically cleaved within the cell to release active tenofovir.
Figure 5:
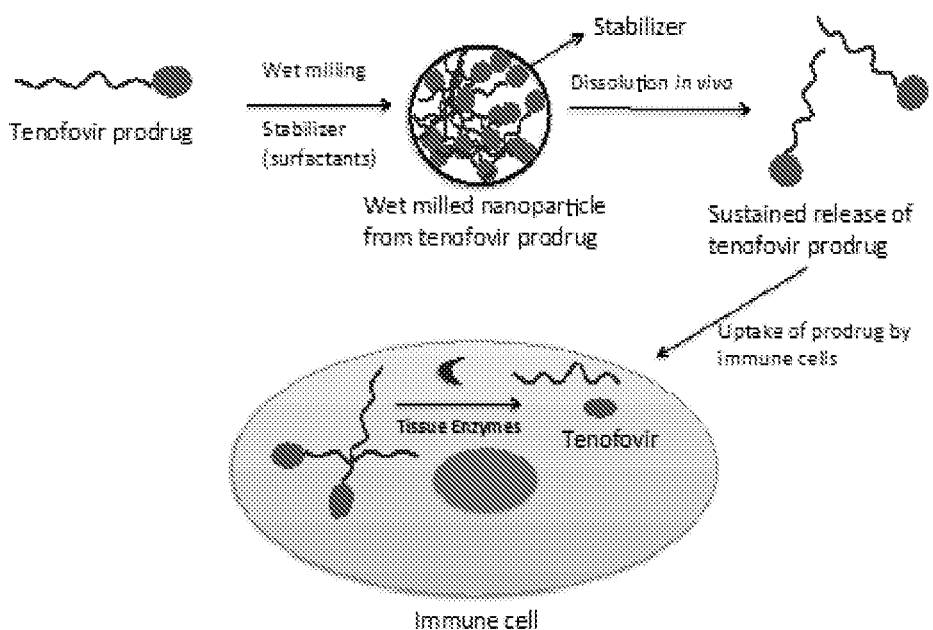
FIG. 5 is a non-limiting scheme of a tenofovir prodrug which is wet-milled in the presence of stabilizers to form wet-milled nanoparticles from the prodrug. Dissolution in vivo results in sustained release of the prodrug which is taken up by immune cells and is enzymatically cleaved within the cell to release active tenofovir.

The hydrophobic parts and the hydrophilic parts of the gelator molecules can interact to form nanostructures (lamellae, sheets, fibers, particles) of gelator molecules. The optional agents may insert and form part of the nanostructures, is entrapped or encapsulated in the gel, or both. In some embodiments, when the gels are hydrogels, the hydrophobic portions of gelators are located in the inner regions of a given nanostructures, and hydrophilic portions are located at the outer surfaces of the nanostructure (see FIG. 2). In some embodiments, when the gels are organogels, the hydrophobic portions of gelators are located in the outer regions of a given nanostructure, and hydrophilic portions are located at the inner surfaces of the nanostructure (see FIG. 2). The nanostructure can have a width of from about three to about five nanometers and a length of several microns (e.g., about one micron, about two microns, about three microns, about four microns, about five microns, about ten microns, about twenty microns, or about twenty five microns) or more. Several tens or hundreds of lamellae can bundle together to form nanostructures, such as fibers and sheet-like structures.

In some embodiments, the nanostructures include nanoparticles, microparticles, micelles, liposomes, vesicles, fibers, sheets, or any combination thereof. In some embodiments, the nanostructures can have a minimum dimension (e.g., a thickness, a width, or a diameter) of 2 nm or more (e.g., 50 nm or more, 100 nm or more, 150 nm or more, 200 nm or more, 250 nm or more, 300 nm or more, 350 nm or more) and/or 400 nm or less (e.g., 350 nm or less, 300 nm or less, 250 nm or less, 200 nm or less, 150 nm or less, 100 nm or less, or 500 nm or less). In some embodiments, the nanostructures (e.g, fibers, sheets) have a length and/or width of several microns (e.g., one micron, two microns, three microns, four microns, five microns, ten microns, twenty microns, or twenty five microns) or more. The nanostructures can aggregate into networks, and/or be in the form of a liquid crystal, emulsion, fibrillar structure, or tape-like morphologies. When the nanostructures are in the form of fibers, the fibers can have a diameter of about 2 nm or more, and can have lengths of hundreds of nanometers or more. In some embodiments, the fibers can have lengths of several microns (e.g., one micron, two microns, three microns, four microns, five microns, ten microns, twenty microns, or twenty five microns) or more.

Degradation (Cleavable Linkage)

In some embodiments, the gelators and/or co-gelators demonstrate responsive release based on linkages contained therein which are formed from degradable chemical bonds (or functional groups) and/or tunable non-covalent association forces (e.g., electrostatic forces, van der Waals, or hydrogen bonding forces). In some embodiments, these linkages are (1) degradable covalent linkage between the hydrophilic segment and the hydrophobic segment of an amphiphile gelator, (2) positioned in a prodrug-type gelator, which upon cleavage releases an active drug, and/or (3) covalent linkage or non-covalent association forces between a gelator and a therapeutic agent. The cleavage or dissociation of these linkages result in (1) more rapid or greater release of the encapsulated or entrapped agents compared to passive diffusion-mediated release of agent; and/or (2) converts prodrug gelator into active drug for release.

Stimuli evoking release includes intrinsic environment in vivo and user-applied stimulation, for example, enzymes, pH, oxidation, temperature, irradiation, ultrasound, metal ions, electrical stimuli, or electromagnetic stimuli. A typical responsive linkage is cleavable through enzyme and/or hydrolysis, based on a chemical bond involving an ester, an amide, an anhydride, a thioester, and/or a carbamate. In some embodiments, phosphate-based linkages can be cleaved by phosphatases or esterase. In some embodiments, labile linkages are redox cleavable and are cleaved upon reduction or oxidation (e.g., —S—S—). In some embodiments, degradable linkages are susceptible to temperature, for example cleavable at high temperature, e.g., cleavable in the temperature range of 37-100° C., 40-100° C., 45-100° C., 50-100° C., 60-100° C., 70-100° C. In some embodiments, degradable linkages can be cleaved at physiological temperatures (e.g., from about 36 to 40° C., about 36° C., about 37° C., about 38° C., about 39° C., about 40° C.). For example, linkages can be cleaved by an increase in temperature. This can allow use of lower dosages, because agents are only released at the required site. Another benefit is lowering of toxicity to other organs and tissues. In certain embodiments, stimuli can be ultrasound, temperature, pH, metal ions, light, electrical stimuli, electromagnetic stimuli, and combinations thereof.

Controlled Release of Anti-Retrovirals and/or Other Agent(s)

The hydrogel or organogels compositions can be prepared for controlled release and/or degradation over a period of time. Degradation may result in release of anti-retrovirals (co-gelators), anti-retrovirals upon cleavage from a prodrug-based gelator, and/or other agents found within the gels. The self-assembled hydrogels or organogels may result in a cumulative release of up to about 10%, about 20%, about 30%, about 40%, about 50%, about 60%, about 70%, about 80%, about 90%, or essentially all of the anti-retroviral and/or other agents in the gels within about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24 hours. In some instances, cumulative release of up to about 10%, about 20%, about 30%, about 40%, about 50%, about 60%, about 70%, about 80%, about 90%, or essentially all of the anti-retroviral and/or other agents in the gels occurs within about 1, about 2, about 3, about 4, about 5, about 6, about 7, about 8, about 9, or about 10 days. In yet other instances, cumulative release of up to about 10%, about 20%, about 30%, about 40%, about 50%, about 60%, about 70%, about 80%, about 90%, or essentially all of the anti-retroviral and/or other agents in the gels occurs within about 1, about 2, about 3, about 4, about 5, about 6, about 7, about 8 weeks or longer. In other instances, cumulative release of up to about 10%, about 20%, about 30%, about 40%, about 50%, about 60%, about 70%, about 80%, about 90%, or essentially all of the anti-retroviral and/or other agents in the gels occurs within about 1, about 2, about 3, about 4, about 5, about 6, about 7, about 8, about 9, about 10, about 11, or about 12 months. In some embodiments where the anti-retrovirals and/or agents in the gels are bound by an enzyme cleavable linker the presence of a stimulus, such as an enzyme, self-assembled gel formed from a gelator with an enzyme-degradable linkage releases the agent more rapidly, compared to the gel in a medium lacking the enzyme. In certain embodiments, the hydrogels or organogels may include one or more control release agents which may increase or decrease the rate of release of the anti-retroviral drugs and/or other agents based on the amount of the control release agent present. An exemplary control release agent is cholesterol.

In some embodiments, the release kinetics of the anti-retroviral drugs can be tuned by including one or more additional co-gelators, such as GRAS amphiphiles described above, which can be used to increase or decrease the rate of release of the drugs and/or other agents in the gels.

Stability

The anti-retroviral drugs (co-gelators) and prodrug-based anti-retrovirals (co-gelators) thereof described present in hydrogels or organogels can remain stable over a period of time.

The stability of the anti-retroviral drugs (co-gelators) and prodrug-based anti-retrovirals (co-gelators) thereof can be determined as percentage of the aforementioned in the hydrogels or organogels after a certain period of time. In certain instances, the anti-retroviral drugs (co-gelators) and prodrug-based anti-retrovirals (co-gelators) present in hydrogels or organogels may remain stable for at least about 1, about 2, about 3, about 4, about 5, about 6, about 7, about 8, about 9, about 10, about 11, or about 12 weeks when stored at room temperature, incubated at 4° C., or stored at 37° C. In certain other instances, the anti-retroviral drugs (co-gelators) and prodrug-based anti-retrovirals (co-gelators) present in hydrogels or organogels may remain stable for at least about 1, about 2, about 3, about 4, about 5, about 6, about 7, about 8, about 9, about 10, about 11, or about 12 months when stored at room temperature, incubated at 4° C., or stored at 37° C. "Remain stable," as used herein refers to a percent loss of the anti-retroviral drugs (co-gelators) and prodrug-based anti-retrovirals (co-gelators) thereof of less than about 10%, about 9%, about 8%, about 7%, about 6%, about 5%, about 4%, about 3%, about 2%, about 1%, about 0.5%, or about 0.1%.

E. Gel Formulations

The self-assembled hydrogel or organogels may be prepared from combinations of gelators, co-gelators, solvents, and co-solvents and according to the methods described herein. The gels may be prepared as powder formulations or as liquid gel formulations.

The gel formulations are typically sterilized or sterile. For example, a sterile formulation can be prepared by first performing sterile filtration of gelators, cationic agents, as well as agents to be encapsulated, followed by processes of preparing the gels in an aseptic environment. Alternatively, all processing steps can be performed under non-sterile conditions, and then terminal sterilization (e.g., gamma or E-beam irradiation) can be applied to the resulting hydrogels or products thereof.

Dry formulations contain lyophilized self-assembled gel compositions where solvent is removed, resulting in xerogels. Xerogels can be in a powder form, which can be useful for maintaining sterility and activity of agents during storage and for processing into desired forms. As xerogels are solvent free, they can have improved shelf-life and can be relatively easily transported and stored. To lyophilize self-assembled gels, the gels can be frozen (e.g., at −80° C.) and vacuum-dried over a period of time to provide xerogels.

Alternatively, a dry formulation contains dry powder components of gelators, cationic agents, one or more therapeutic agents, which are stored in separate containers, or mixed at specific ratios and stored. In some embodiments, suitable aqueous and organic solvents are included in additional containers. In some embodiments, dry powder components, one or more solvents, and instructions on procedures to mix and prepare assembled nanostructures are included in a kit.

Liquid gel formulations contain self-assembled gel composition suspended in a liquid pharmaceutical carrier. In some forms, self-assembled gel is suspended or re-suspended in aqueous media for ease of administration and/or reaching a desired concentration for minimizing toxicity.

The liquid formulations described may be isotonic relative to body fluids and of approximately the same pH, ranging from about pH 4.0 to about pH 8.0, more preferably from about pH 6.0 to about pH 7.6. The liquid pharmaceutical carrier can include one or more physiologically compatible buffers, such as a phosphate or bicarbonate buffers. One skilled in the art can readily determine a suitable saline content and pH for an aqueous solution that is suitable for an intended route of administration.

In some instances, the liquid formulations may include one or more suspending agents, such as cellulose derivatives, sodium alginate, polyvinylpyrrolidone, gum tragacanth, or lecithin. Liquid formulations may also include one or more preservatives, such as ethyl or n-propyl p-hydroxybenzoate.

III. Methods of Making

1. Methods of Preparing Gels

The liquid medium for the gelators to form self-assembled gels generally include a one-solvent system (typically for organogels) or a two-solvent system (typically for hydrogels) of an organic solvent and water (or an aqueous salt solution), or an aqueous-organic mixture solvent system.

a. Hydrogels

In one embodiment for forming hydrogels, a method of preparing a self-assembled hydrogel includes the steps of:

(1) Adding an amount of one or more GRAS amphiphiles (gelators) to a suitable container (such as a vial);

(2) Adding one or more anti-retroviral drugs, such as tenofovir alafenamide (TAF), (as a co-gelator) to the same container;

(3) Adding a first solvent (such as, hexyl butyrate, glycerol, or propylene glycol) to the vial;

(4) Heating the mixture until dissolution of the amphiphile(s) and the one or more anti-retroviral drugs;

(5) Adding a second solvent (such as water or an aqueous solution) to the container and heating the container until the mixture formed becomes a uniform solution; and (6) Allowing the mixture to cool to room temperature such that gelation occurs, typically within 15-20 minutes.

Gelation is achieved when following cooling the uniform mixture of step (6) becomes a self-supporting mass (i.e., a hydrogel). Typically the hydrogel formed is a viscous gel stable which is stable to inversion (e.g., resists flow when inverted). Gelation takes place as the heated gelation solution cools (typically to room temperature) or is cooled (such as controlled cooled at a determined rate of cooling). Leaving the gel on a stable surface for about 15-20 mins, about 15-30 mins, about 15-40 mins, about 15-50 mins, 1 about 5-60 mins, or about one to about two hours at room temperature results in a consistent self-supporting hydrogel.

The hydrogel may be characterized by methods including, but not limited to, optical or electron microscopy. The hydrogels may be characterized as being formed of ordered assembled micro- or nano-structures (i.e., (nano)fibrous/fiber-like, lamellar, tape-like, and/or vesicular). The hydrogels may demonstrate no precipitates or substantially no precipitates by inspection ("substantially," refers to less 10%, 9%, 8%, 7%, 6%, 5%, 4%, 3%, 2%, 1%, 0.5%, or 0.1% precipitates present by weight).

In some embodiments of the above method, the heating in steps (4) and (5) are each independently carried out at temperatures ranging from between about 30-100° C., about 40-100° C., about 50-100° C., about 60-100° C., about 70-100° C., about 90-100° C., about 30-90° C., about 40-90° C., about 50-90° C., about 60-90° C., about 70-90° C., about 80-90° C., about 40-80° C., about 50-80° C., about 60-80° C., about 70-80° C., about 30-70° C., about 40-70° C., about 50-70° C., about 60-70° C., about 30-60° C., about 40-60° C., about 50-60° C., about 30-50° C., or about 40-50° C. In some embodiments, the heating in steps (4) and (5) is carried out in the temperature range of between about 60-80° C.

The one or more anti-retrovirals (co-gelators) may be selected without limit from tenofovir and derivatives thereof, tenofovir alafenamide, cabotegravir, rilpivirine, emtricitabine, abacavir, lamivudine, adefovir, or other known anti-retrovirals which are commercially available, or derivatives of any of those listed herein. In some embodiments, the one or more anti-retrovirals may be pharmaceutically acceptable salts of anti-retrovirals of tenofovir and derivatives thereof, tenofovir alafenamide, cabotegravir, rilpivirine, emtricitabine, abacavir, lamivudine, adefovir, or other known anti-retrovirals which are commercially available, or derivatives of any of those listed herein. Methods of preparing pharmaceutically acceptable salts of anti-retroviral drugs are known. In some embodiments, the anti-retroviral is a fumarate salt of tenofovir alafenamide. The hydrogels may demonstrate loading efficiencies of the one or more anti-retroviral drugs when the loading amounts of the drugs are up to about 90 wt/wt %, about 80 wt/wt %, about 70 wt/wt %, about 60 wt/wt %, about 50 wt/wt %, about 45 wt/wt %, about 40 wt/wt %, about 35 wt/wt %, about 30 wt/wt %, about 25 wt/wt %, about 20 wt/wt %, about 15 wt/wt %, about 10 wt/wt %, or about 5 wt/wt %. In some embodiments, the loading of the one or more anti-retroviral drugs in the resulting hydrogels are about 1 mg, about 5 mg, about 10 mg, about 20 mg, about 30 mg, about 40 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, or about 1000 mg per mL of hydrogel. In certain embodiments, the loading of the one or more anti-retroviral drugs in the resulting hydrogels is in the range of between about 100-1000 mg per mL of hydrogel when the loading amounts are greater than or equal to 50%.

The organic solvent can be selected based on the solubility of the GRAS gelators and co-gelators therein, its polarity, hydrophobicity, water-miscibility, and in some cases the acidity. Suitable organic solvents include water-miscible solvent, or solvent that has an appreciable water solubility (e.g., greater than 5 g/100 g water), e.g., propylene glycol, dipropylene glycol, N-Methyl-2-pyrrolidone (NMP), hexyl butyrate, glycerol, acetone, dimethylformamide (DMF), tetrahydrofuran, dioxane, acetonitrile, alcohols such as ethanol, methanol or isopropyl alcohol, as well as low molecular weight polyethylene glycol (e.g., 1 kDa PEG which melts at 37° C.), or any combination thereof. In other forms, the self-assembled gel compositions can include a polar or non-polar solvent, such as water, benzene, toluene, carbon tetrachloride, acetonitrile, glycerol, 1,4-dioxane, dimethyl sulfoxide, ethylene glycol, methanol, chloroform, hexane, acetone, benzyl alcohol, N, N'-dimethyl formamide, ethanol, isopropyl alcohol, butyl alcohol, pentyl alcohol, tetrahydrofuran, xylene, mesitylene, and/or any combination thereof.

The amount of an organic solvent present in the hydrogels according the above method is generally less than about 50%, about 40%, about 30%, about 25%, about 20%, about 15%, or about 10% by vol/vol of the total volume used in the preparation of the hydrogel. In other instances, the amount of an organic solvent present in the hydrogels according the above method is generally less than about 50%, about 40%, about 30%, about 25%, about 20%, about 15%, or about 10% by wt/vol of the total volume used in the preparation of the hydrogel.

The second solvent is typically water which may be sterilized and selected from distilled water, de-ionized water, pure or ultrapure water. In some instances the second solvent is an aqueous solution such as saline, other physiologically acceptable aqueous solutions containing salts and/or buffers, such as phosphate buffered saline (PBS), Ringer's solution, and isotonic sodium chloride, or any other aqueous solution acceptable for administration to a subject, such as an animal or human. The amounts of the second solvent are typically based on the amounts of the first organic solvent used wherein the selected total volume or weight percentage of organic solvent(s) determined the volume or weight percentage of the water or aqueous solution (i.e., if 30 v/v % of organic solvent then 70 v/v % water).

The resulting hydrogels described may be isotonic relative to body fluids and of approximately the same pH, ranging from about pH 4.0 to about pH 8.0, more preferably from about pH 6.0 to about pH 7.6, even more preferably from about pH 7.0 to about pH 7.6.

GRAS gelators, anti-retroviral drugs (co-gelators), organic solvents, and water are selected at an appropriate gelator concentration and appropriate volume and ratio of the aqueous-organic mixture solvent system, or both, to form self-supporting hydrogels.

b. Organogels

In one embodiment for forming organogels, a method of preparing a self-assembled organogel includes the steps of:

(1) Adding an amount of one or more GRAS amphiphiles (gelators) to a suitable container (such as a vial);

(2) Adding one or more anti-retroviral drugs, such as tenofovir alafenamide (TAF), (as a co-gelator) to the same container;

(3) Adding one or more oil-based solvents (such as, olive oil, castor oil, corn oil, sesame oil, soybean oil) to the vial;

(4) Heating the mixture until dissolution of the amphiphile(s) and the one or more anti-retroviral drugs;

(5) Allowing the mixture to cool to room temperature such that gelation occurs, typically within 15-20 minutes.

Gelation is achieved when following cooling the uniform mixture of step (5) becomes a self-supporting mass (i.e., an organogel). Typically the organogel formed is a viscous gel stable which is stable to inversion (e.g., resists flow when inverted). Gelation takes place as the heated gelation solution cools (typically to room temperature) or is cooled (such as controlled cooled at a determined rate of cooling). Leaving the gel on a stable surface for about 15-20 mins, about 15-30 mins, about 15-40 mins, about 15-50 mins, about 15-60 mins, or about one to two hours at room temperature results in a consistent self-supporting organogel.

The organogel may be characterized by methods including, but not limited to, optical or electron microscopy. The organogels may be characterized as being formed of ordered assembled micro- or nano-structures (i.e., (nano)fibrous/fiber-like, lamellar, tape-like, and/or vesicular). The organogels may demonstrate no precipitates or substantially no precipitates by inspection ("substantially," refers to less 10%, 9%, 8%, 7%, 6%, 5%, 4%, 3%, 2%, 1%, 0.5%, or 0.1% precipitates present by weight).

In some embodiments of the above method, the heating in step (4) is carried out at temperatures ranging from between about 30-100° C., about 40-100° C., about 50-100° C., about 60-100° C., about 70-100° C., about 90-100° C., about 30-90° C., about 40-90° C., about 50-90° C., about 60-90° C., about 70-90° C., about 80-90° C., about 40-80° C., about 50-80° C., about 60-80° C., about 70-80° C., about 30-70° C., about 40-70° C., about 50-70° C., about 60-70° C., about 30-60° C., about 40-60° C., about 50-60° C., about 30-50° C., or about 40-50° C. In some embodiments, the heating in step (4) is carried out in the temperature range of between about 60-80° C.

The one or more anti-retrovirals (co-gelators) may be selected without limit from tenofovir and derivatives thereof, tenofovir alafenamide, cabotegravir, rilpivirine, emtricitabine, abacavir, lamivudine, adefovir, or other known anti-retrovirals which are commercially available, or derivatives of any of those listed herein. In some embodiments, the one or more anti-retrovirals may be pharmaceutically acceptable salts of anti-retrovirals of tenofovir and derivatives thereof, tenofovir alafenamide, cabotegravir, rilpivirine, emtricitabine, abacavir, lamivudine, adefovir, or other known anti-retrovirals which are commercially available, or derivatives of any of those listed herein. Methods of preparing pharmaceutically acceptable salts of anti-retroviral drugs are known. In some embodiments, the anti-retroviral is a fumarate salt of tenofovir alafenamide. The organogels may demonstrate loading efficiencies of the one or more anti-retroviral drugs when the loading amounts of the drugs are up to about 90 wt/wt %, about 80 wt/wt %, about 70 wt/wt %, about 60 wt/wt %, about 50 wt/wt %, about 45 wt/wt %, about 40 wt/wt %, about 35 wt/wt %, about 30 wt/wt %, about 25 wt/wt %, about 20 wt/wt %, about 15 wt/wt %, about 10 wt/wt %, or about 5 wt/wt %. In some embodiments, the loading of the one or more anti-retroviral drugs in the resulting organogels are about 1 mg, about 5 mg, about 10 mg, about 20 mg, about 30 mg, about 40 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, or about 1000 mg per mL of organogel. In certain embodiments, the loading of the one or more anti-retroviral drugs in the resulting organogels is in the range of between about 100-1000 mg per mL of organogel when the loading amounts are greater than or equal to 50%.

The oil-based solvents can be selected based on the solubility of the GRAS gelators and co-gelators therein. Suitable oil-based solvents include, but are not limited to, olive oil, castor oil, corn oil, sesame oil, soybean oil and any blends or combinations thereof. In some embodiments, blends of any of the aforementioned oils may be formed wherein the blends contain up to at least about 10%, about 20%, about 30%, about 40%, about 50%, about 60%, about 70%, about 80%, about 90%, about 91%, about 92%, about 93%, about 94%, about 95%, about 96%, about 97%, about 98%, or about 99% castor oil.

The resulting organogels described may be isotonic relative to body fluids and of approximately the same pH, ranging from about pH 4.0 to about pH 8.0, more preferably from about pH 6.0 to about pH 7.6, even more preferably from about pH 7.0 to about pH7.6.

Gelators, anti-retroviral co-gelators, and oil-based solvents are selected at an appropriate gelator concentration and appropriate volume and ratio of the oil-based solvent system, or both, to form self-supporting organogels.

c. Gels Formed from Anti-Retroviral Prodrugs

In some embodiments gels are formed using the anti-retroviral prodrugs described above.

1. Prodrug-Based Hydrogels

A non-limiting method of preparing a self-assembled hydrogel includes the steps of:

(1) Adding an amount of one or more organic solvents (such as DMSO, NMP, or propylene glycol) to a suitable container (such as a vial);

(2) Adding one or more anti-retroviral prodrugs (as a gelator) to the same container;

(3) Heating the mixture until dissolution of the one or more anti-retroviral prodrugs;

(4) Adding a second solvent which is water (or an aqueous solution) to the same container;

(5) Heating the mixture to ensure dissolution of the one or more anti-retroviral prodrugs;

(6) Allowing the mixture to cool to room temperature such that gelation occurs, typically within 15-20 minutes.

Gelation is achieved when following cooling the uniform mixture of step (6) becomes a self-supporting mass (i.e., a hydrogel). Typically the hydrogel formed is a viscous gel stable which is stable to inversion (e.g., resists flow when inverted). Gelation takes place as the heated gelation solution cools (typically to room temperature) or is cooled (such as controlled cooled at a determined rate of cooling). Leaving the gel on a stable surface for about 15-20 mins, about 15-30 mins, about 15-40 mins, about 15-50 mins, about 15-60 mins, or about one to two hours at room temperature results in a consistent self-supporting hydrogel.

The prodrug-based hydrogel may be characterized by methods including, but not limited to, optical or electron microscopy. The hydrogels may be characterized as being formed of ordered assembled micro- or nano-structures (i.e., (nano)fibrous/fiber-like, lamellar, tape-like, and/or vesicular). The hydrogels may demonstrate no precipitates or substantially no precipitates by inspection ("substantially," refers to less 10%, 9%, 8%, 7%, 6%, 5%, 4%, 3%, 2%, 1%, 0.5%, or 0.1% precipitates present by weight).

In some embodiments of the above method, the heating in steps (3) and (5) are each independently carried out at temperatures ranging from between about 30-100° C., about 40-100° C., about 50-100° C., about 60-100° C., about 70-100° C., about 90-100° C., about 30-90° C., about 40-90° C., about 50-90° C., about 60-90° C., about 70-90° C., about 80-90° C., about 40-80° C., about 50-80° C., about 60-80° C., about 70-80° C., about 30-70° C., about 40-70° C., about 50-70° C., about 60-70° C., about 30-60° C., about 40-60° C., about 50-60° C., about 30-50° C., or about 40-50° C. In some embodiments, the heating in steps (3) and (5) is carried out in the temperature range of between about 60-80° C.

The one or more anti-retroviral prodrugs (gelators) may be synthesized according to the methods described above. In some instances, the prodrugs (gelators) are compounds according to any one of Formulae (I)-(III) or any combination thereof. The hydrogels may demonstrate loading efficiencies of the one or more anti-retroviral prodrugs when the loading amounts of the prodrugs are up to about 90 wt/wt %, about 80 wt/wt %, about 70 wt/wt %, about 60 wt/wt %, about 50 wt/wt %, about 45 wt/wt %, about 40 wt/wt %, about 35 wt/wt %, about 30 wt/wt %, about 25 wt/wt %, about 20 wt/wt %, about 15 wt/wt %, about 10 wt/wt %, about 5 wt/wt %, about 4 wt/wt %, about 3 wt/wt %, about 2 wt/wt %, about 1 wt/wt %. In some embodiments, the amount of prodrug gelator is greater than about 3 wt/wt %. In some embodiments, the loading of the one or more anti-retroviral prodrugs in the resulting hydrogels are about 1 mg, about 5 mg, about 10 mg, about 20 mg, about 30 mg, about 40 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, or about 1000 mg per mL of hydrogel. In certain embodiments, the loading of the one or more anti-retroviral prodrugs in the resulting hydrogels is in the range of between about 100-1000 mg per mL of hydrogel when the loading amounts are greater than or equal to 50%.

The prodrugs typically contain an enzymatically cleavable linker which is cleaved upon exposure to an appropriate enzyme, as described in detail in the disclosure herein.

The organic solvent(s) can be selected based on the solubility of the GRAS gelators and co-gelators therein, its polarity, hydrophobicity, water-miscibility, and in some cases the acidity. Suitable organic solvents include water-miscible solvent, or solvent that has an appreciable water solubility (e.g., greater than 5 g/100 g water), e.g., propylene glycol, dimethylformamide (DMF), dimethyl sulfoxide (DMSO), propylene glycol, dipropylene glycol, hexyl butyrate, glycerol, acetone, tetrahydrofuran, dioxane, acetonitrile, alcohols such as ethanol, methanol or isopropyl alcohol, as well as low molecular weight polyethylene glycol (e.g., 1 kDa PEG which melts at 37° C.), or any combination thereof. In other forms, the self-assembled gel compositions can include a polar or non-polar solvent, such as water, benzene, toluene, carbon tetrachloride, benzyl alcohol, acetonitrile, glycerol, 1,4-dioxane, dimethyl sulfoxide, ethylene glycol, methanol, chloroform, hexane, acetone, N, N'-dimethyl formamide, ethanol, isopropyl alcohol, butyl alcohol, pentyl alcohol, tetrahydrofuran, xylene, mesitylene, and/or any combination thereof.

The amount of an organic solvent present in the hydrogels according the above method is generally less than about 50%, about 40%, about 30%, about 25%, about 20%, about 15%, or about 10% by vol/vol of the total volume used in the preparation of the hydrogel. In other instances, the amount of an organic solvent present in the hydrogels according the above method is generally less than about 50%, about 40%, about 30%, about 25%, about 20%, about 15%, or about 10% by wt/vol of the total volume used in the preparation of the hydrogel.

The second solvent is typically water which may be sterilized and selected from distilled water, de-ionized water, pure or ultrapure water. In some instances the second solvent is an aqueous solution such as saline, other physiologically acceptable aqueous solutions containing salts and/or buffers, such as phosphate buffered saline (PBS), Ringer's solution, and isotonic sodium chloride, or any other aqueous solution acceptable for administration to a subject, such as an animal or human. The amounts of the second solvent are typically based on the amounts of the first organic solvent used wherein the selected total volume or weight percentage of organic solvent(s) determined the volume or weight percentage of the water or aqueous solution (i.e., if 25 v/v % of organic solvent then 75 v/v % water).

The resulting hydrogels described may be isotonic relative to body fluids and of approximately the same pH, ranging from about pH 4.0 to about pH 8.0, more preferably from about pH 6.0 to about pH 7.6, even more preferably from about pH 7.0 to about pH 7.6.

Anti-retroviral prodrugs (gelators), organic solvents, and water are selected at an appropriate gelator concentration and appropriate volume and ratio of the aqueous-organic mixture solvent system, or both, to form self-supporting hydrogels.

2. Prodrug-Based Organogels

In some other embodiments, a non-limiting method of preparing a self-assembled hydrogel includes the steps of:

(1) Adding one or more anti-retroviral prodrugs (as a gelator) to a same container, such as a vial;

(2) Adding one or more oil-based solvents (such as olive oil, castor oil, or soybean oil) to the same container;

(3) Heating the mixture to ensure dissolution of the one or more anti-retroviral prodrugs;

(4) Allowing the mixture to cool to room temperature such that gelation occurs, typically within 15-20 minutes.

Gelation is achieved when following cooling the uniform mixture of step (5) becomes a self-supporting mass (i.e., an organogel). Typically the organogel formed is a viscous gel stable which is stable to inversion (e.g., resists flow when inverted). Gelation takes place as the heated gelation solution cools (typically to room temperature) or is cooled (such as controlled cooled at a determined rate of cooling). Leaving the gel on a stable surface for about 15-20 mins, about 15-30 mins, about 15-40 mins, about 15-50 mins, about 15-60 mins, or about one to two hours at room temperature results in a consistent self-supporting organogel.

The organogel may be characterized by methods including, but not limited to, optical or electron microscopy. The organogels may be characterized as being formed of ordered assembled micro- or nano-structures (i.e., (nano)fibrous/fiber-like, lamellar, tape-like, and/or vesicular). The organogels may demonstrate no precipitates or substantially no precipitates by inspection ("substantially," refers to less 10%, 9%, 8%, 7%, 6%, 5%, 4%, 3%, 2%, 1%, 0.5%, or 0.1% precipitates present by weight).

In some embodiments of the above method, the heating in step (3) is carried out at temperatures ranging from between about 30-100° C., about 40-100° C., about 50-100° C., about 60-100° C., about 70-100° C., about 90-100° C., about 30-90° C., about 40-90° C., about 50-90° C., about 60-90° C., about 70-90° C., about 80-90° C., about 40-80° C., about 50-80° C., about 60-80° C., about 70-80° C., about 30-70° C., about 40-70° C., about 50-70° C., about 60-70° C., about 30-60° C., about 40-60° C., about 50-60° C., about 30-50° C., or about 40-50° C. In some embodiments, the heating in step (3) is carried out in the temperature range of between about 60-80° C.

The one or more anti-retroviral prodrugs (gelators) may be synthesized according to the methods described above. In some instances, the prodrugs (gelators) are compounds according to any one of Formulae (I)-(III) or any combination thereof. The organogels may demonstrate loading efficiencies of the one or more anti-retroviral drugs when the loading amounts of the drugs are up to about 90 wt/wt %, about 80 wt/wt %, about 70 wt/wt %, about 60 wt/wt %, about 50 wt/wt %, about 45 wt/wt %, about 40 wt/wt %, about 35 wt/wt %, about 30 wt/wt %, about 25 wt/wt %, about 20 wt/wt %, about 15 wt/wt %, about 10 wt/wt %, about 5 wt/wt %, about 4 wt/wt %, about 3 wt/wt %, about 2 wt/wt %, about 1 wt/wt %. In some embodiments, the amount of prodrug gelator is greater than about 3 wt/wt %. In some embodiments, the loading of the one or more anti-retroviral prodrugs in the resulting organogels are about 1 mg, about 5 mg, about 10 mg, about 20 mg, about 30 mg, about 40 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, or about 1000 mg per mL of organogel. In certain embodiments, the loading of the one or more anti-retroviral prodrugs in the resulting organogels is in the range of between about 100-1000 mg per mL of organogel when the loading amounts are greater than or equal to 50%.

The oil-based solvents can be selected based on the solubility of the GRAS gelators and co-gelators therein. Suitable oil-based solvents include, but are not limited to, olive oil, castor oil, corn oil, sesame oil, soybean oil and any blends or combinations thereof. In some embodiments, blends of any of the aforementioned oils may be formed wherein the blends contain up to at least about 10%, about 20%, about 30%, about 40%, about 50%, about 60%, about 70%, about 80%, about 90%, about 91%, about 92%, about 93%, about 94%, about 95%, about 96%, about 97%, about 98%, or about 99% castor oil.

The resulting organogels described may be isotonic relative to body fluids and of approximately the same pH, ranging from about pH 4.0 to about pH 8.0, more preferably from about pH 6.0 to about pH 7.6, even more preferably from about pH 7.0 to about pH 7.6.

Anti-retroviral prodrug gelators and oil-based solvents are selected at an appropriate gelator concentration and appropriate volume and ratio of the oil-based solvent system, or both, to form self-supporting organogels.

2. Optional Gel Purification

Distillation, filtration, dialysis, centrifugation, other solvent exchange techniques, vacuum, drying, or lyophilization may be used in one or more repeated processes to remove unencapsulated excess agent and organic solvent from the gels (hydrogels or organogels described above) to below the stated limit of pharmaceutical product requirements.

Generally a purification medium is one suitable for administration, such that the solvent of the gel is at least partially replaced with the purification medium.

Generally, a process to make the self-assembled gel composition includes combining gelators, cationic agents, therapeutic agents, and solvents to form a mixture; heating or sonicating the mixture; stirring or shaking the mixture for a time sufficient to form a homogeneous solution; and cooling the homogenous solution for a time sufficient to enable the formation of self-assembled gel compositions.

3. Suspension into a Fibrous Mixture and Processing into Particles

The self-assembled hydrogels or organogels in some embodiments are suspended in a pharmaceutically acceptable form for ease of administration to a patient (e.g., by drinking or injection) and/or to provide a desired drug concentration to control toxicity.

In some forms, the bulk gels are suspended in water, phosphate buffered saline, or other physiological saline, which is homogenized or sonicated to break up the bulk gel into particles (micro and/or nanoparticles) which retain the fibrous nanostructures formed in the bulk gel.

In some embodiments, the bulk gel and the prodrugs may be wet milled to produce particles. Wet (nano)milling may afford several advantages over use of non-wet milled gels and prodrugs including, but not limited to, scalability, increase uptake by immune cells, improvements in sustained release, and higher drug concentrations (since wet milled particles generally have no matrix material). These particles may be microparticles, nanoparticles, or combinations thereof. In some instances, wet milling occurs in the presence of suitable excipients selected from, but not limited to cellulose, lactose, starch, polysorbates, or combinations thereof. Methods of wet milling are known.

In some embodiments, the nanoparticles and/or microparticles have a minimum dimension (e.g., a thickness, a width, or a diameter) of 2 nm or more (e.g., 50 nm or more, 100 nm or more, 150 nm or more, 200 nm or more, 250 nm or more, 300 nm or more, 350 nm or more, 500 nm or more, 1,000 nm or more, 5,000 nm or more, or 10,000 nm or more) and/or 400 nm or less (e.g., 10,000 nm or less, 5,000 nm or less, 1,000 nm or less, 500 nm or less, 350 nm or less, 300 nm or less, 250 nm or less, 200 nm or less, 150 nm or less, 100 nm or less, or 500 nm or less). The particles may aggregate into networks, and/or be in the form of a liquid crystal, emulsion, or other types of morphologies. It is believed that the size of the wet milled particles can be used to tune release kinetics of the anti-retroviral drugs or other agents in the gels where large sized particles (more than 5000 nm) demonstrate slower release than small sized particles (less than 750 nm) and medium sized particles (750-5000 nm) show release rates which are intermediate to the small and large particles.

The particles can be collected, stored, and reconstituted prior to use in a suitable medium and at an appropriate concentration for administration. Different types of gel particles loaded with different amounts or types of therapeutic agents may be combined.

In some embodiments, particles are nanoparticles having a hydrodynamic diameter between 100 nm and 990 nm, preferably between 500 nm and 900 nm, and the nanoparticles maintain at least 50, 60, 70 or 80% of the size in serum over a period of at least two hours.

In other embodiments, particles are microparticles having a diameter ranging from 1 μm to a couple hundred millimeters.

4. Sterilization

A sterile formulation is prepared by first performing sterile filtration of the process solutions (e.g., drug and gelator solutions), followed by gel preparation, suspension, purification and lyophilization under aseptic procession conditions. Alternatively, all processing steps can be performed under non-sterile conditions, and then terminal sterilization (e.g., gamma or E-beam irradiation) can be applied to the lyophilized hydrogel product. Sterile solution for resuspension can also be prepared using similar methods.

IV. Methods of Use

The gels, formulations thereof, and/or milled particles thereof can be administered through various known methods. The gels, formulations thereof, and particles can be administered subcutaneously, intramuscularly, intravenously, orally, via inhalation, transdermally, intraperitoneally, intravaginally, intrarectally and intravesically. In certain instances, the gels, formulations thereof, and/or particles thereof described herein are well-suited for delivery by injection. In yet other instances, the gels, formulations thereof, and/or particles thereof may be loaded onto porous implants which can be implanted (and removed in needed)

The gels, formulations thereof, and/or milled particles thereof can exhibit controlled release of active agents (such as anti-retroviral drugs, prodrugs thereof, or other agents) over long course of time (such as 8-12 weeks or more) with minimal prolonged sub-therapeutic PK tail, and therefor can be used as long acting therapeutics for treating viral infectious diseases, such as HIV infection, hepatitis B, and others, such as influenza.

In some instances, the gels, formulations thereof, and/or particles thereof described herein are biodegradable, exhibit minimal toxicity when they degrade, and can deliver active agent (such as anti-retroviral drugs, prodrugs thereof, or other agents) at doses as high as about 1000 mg formulated in about 2-4 ml volumes, with loading efficiencies ranging from about 10-20, about 10-30, about 10-40, or about 10-50 wt/wt % or greater.

In some embodiments, optimal therapeutic effect can be achieved with a dosing frequency of one subcutaneous or intramuscular injection of the gels, formulations thereof, and/or milled particles thereof every about 1-2, about 1-3, about 1-4, about 1-5, about 1-6, about 1-7, about 1-8, about 1-9, about 1-10, about 1-11, or about 1-12 weeks or more. The drug or the prodrug and the other agents are subsequently released through dissolution, hydrolytic or other forms of degradation or in response to a stimulus, such as a specific enzyme.

In some forms, the self-assembled gels, formulations, or particles thereof can be used in a methods of preventing or treating one or more symptoms of viral diseases or disorders in a subject by administering an effective amount of the self-assembled gel composition to deliver an effective amount of therapeutic, prophylactic, or diagnostic agents.

Benefits of the methods and materials described herein include higher drug loading, as high as 60% w/w. Additionally, the optimal conditions for self-assembly of each type of prodrug, including solvents, gelation time, concentrations for the prodrugs of anti-retrovirals, including TAF, have been identified.

The present invention will be further understood by reference to the following non-limiting examples.

EXAMPLES

Example 1: Prodrug of Tenofovir (Octyl hydrogen ((((R)-1-(6-amino-9H-purin-9-yl)oxy)methyl)phosphonate)

Methods:

A prodrug of tenofovir was prepared as follows. To an oven dried round bottom flask was added 100 mg (1 eq, 0.35 mmol) ((R)-9-(2-Phosphonomethoxy propyl)adenine), 75 mg (1.05 eq, 0.37 mmol) N, N'dicyclohexylcarbodiimide, 4.3 mg (0.1 eq, 0.035 mmol) 4-dimethylaminopyridine, 226 mg (5 eq, 1.74 mmol) 1-octanol and 5 mL pyridine. The solution was stirred vigorously at 100° C. for 20 hours. The reaction was cooled to room temperature and the mixture was diluted with 1 mM NaOH (aq) solution and chloroform. The aqueous layer was isolated, acidified to pH<2 with 12M HCl and filtered. The isolate was concentrated under reduced pressure to afford the desired compound as a white solid, resulting in 58 mg of the prodrug with a 41% yield.

Results:

The synthesis and purity of the prodrug were confirmed by $^1$H-NMR: 400 MHz, d-DMSO, δ (m, int), 8.21 (s, 1H), 8.16 (s, 1H), 7.64 (s, 2H), 4.31-4.15 (m, 2H), 3.96-3.92 (m, 2H), 3.79-3.75 (m, 3H), 1.47 (m, 2H), 1.22 (m, 12H), 1.06 (d, 3H), 0.84 (t, 3H). Elemental analysis: C, 51.12; H, 7.57; N, 17.53; 0, 16.02; and P, 7.75.

The chemical structure of the resulting tenofovir prodrug (of Formula (I)) is shown below:

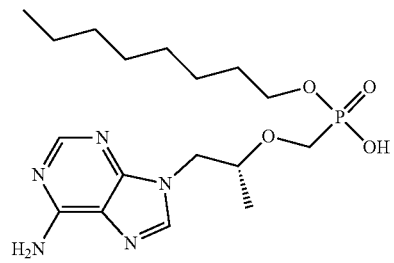 [SMILES: CCCCCCCCOP(=O)(O)CO[C@H](C)Cn1cnc2c(N)ncnc21]

Example 2: Synthesis of Tenofovir Prodrug Dimer

To an oven dried round bottom flask is added 1 equivalent of ((R)-9-(2-Phosphonomethoxypropyl)adenine), 1.05 equivalents of Carbodiimide coupling reagent (typically N,N'-dicyclohexylcarbodiimide or N,N'-diisopropylcarbodiimide), 0.1 equivalents of 4-dimethylaminopyridine, 5 equivalents of a primary terminal monoprotected alkyl diol (e.g. 1-triethtylsilylhexan-6-ol). The material is suspended in an organic nitrogenous base (typically dry pyridine, dimethylformamide, N-methyl-2-pyrrolidone or triethylamine), which creates a white suspension. This suspension is heated to 100° C. and stirs vigorously for 5-72 hours and is then cooled to room temperature. To the reaction mixture is added 75 mL chloroform and 75 mL 1 mM NaOH (aq). The aqueous layer is isolated and 12M HCl (aq) is added dropwise until pH<2. The material is washed with 5% HCl (aq), filtered and the filtrate is dried under reduced pressure to afford the intermediate compound. The material is dissolved in methanol and stirs with 5 eq. potassium carbonate for 12-24 hours. The reaction mixture is filtered then concentrated under reduced pressure, redissolved in chloroform and washed with water then brine. The material is dried with sodium sulfate and concentrated under reduced pressure.

Then, to an oven dried round bottom flask is added 1 equivalent of the nucleotide analogue (typically tenofovir, and usually the same analog as used previously in this scheme), 1.05 equivalents of Carbodiimide coupling reagent (typically N,N'-dicyclohexylcarbodiimide or N,N'-diisopropylcarbodiimide), 0.1 equivalents of 4-dimethylaminopyridine, 1 equivalent of the intermediate is added. The material is suspended in an organic nitrogenous base (typically dry pyridine, dimethylformamide, N-methyl-2-pyrrolidone or triethylamine), which creates a white suspension. This suspension is heated to 100° C. and stirs vigorously for 5-72 hours and is then cooled to room temperature. To the reaction mixture is added 75 mL chloroform and 75 mL 1 mM NaOH (aq). The aqueous layer is isolated and 12M HCl (aq) is added dropwise until pH<2. The material is washed with 5% HCl (aq), filtered and the filtrate is dried under reduced pressure to afford the desired product in overall modest yield.

Example 3: Prodrugs of Tenofovir (Octadecyl hydrogen((((R)-1-(6-amino-9H-parin-9-yl)propan-2 yl)oxy)methyl)phosphonate & Decyl Hydrogen ((((R)-1-(6-amino-9H-parin-9-yl)propan-2-yl)oxy) methyl)phosphonate)

Methods:

(1) For octadecyl hydrogen((((R)-1-(6-amino-9H-purin-9-yl)propan-2 yl)oxy)methyl)phosphonate: One equivalent of tenofovir was added to a dry round bottom flask or scintillation vial. 1.3 equivalents of a haloalkane (1-Iodooctadecane) was then added to the same flask with 3 equivalents of triethylamine (TEA). 93 equivalents of the solvent Dimethylformamide (DMF) were added to the flask. The flask was capped and placed under a nitrogen atmosphere. The flask was heated to 80° C. and allowed to stir for 18 hours. After 18 hours flask was allowed to cool to room temperature and the reaction mixture was separated via chromatography. Product fractions were collected and concentrated under reduced pressure to recover desired prodrug target compound.

(2) For decyl hydrogen ((((R)-1-(6-amino-9H-purin-9-yl)propan-2-yl)oxy)methyl)phosphonate: One equivalent of tenofovir was added to a dry round bottom flask or scintillation vial. 1.3 equivalents of haloalkane (1-Iododecane) was then added to the same flask with 3 equivalents of triethylamine (TEA). 93 equivalents of the solvent Dimethylformamide (DMF) was then added to the flask. The flask was capped and placed under a nitrogen atmosphere. Flask was heated to 80° C. and allowed to stir for 18 hours. After 18 hours flask was allowed to cool to room temperature and the reaction mixture was separated via chromatography. Product fractions are collected and concentrated under reduced pressure to recover desired compound.

Results:

The isolated compound of the first synthesis above was characterized by $^1$H NMR and was consistent with presence of desired octadecyl hydrogen ((((R)-1-(6-amino-9H-purin-9-yl)propan-2-yl)oxy)methyl)phosphonate target. The appearance of a triplet peak at 0.9 ppm corresponds to the hydrogens of the terminal methyl group on the inserted chain and the appearance of multiple peaks at 1.26 ppm corresponded to hydrogens found in long chain. The chemical structure of the prodrug is as follows:

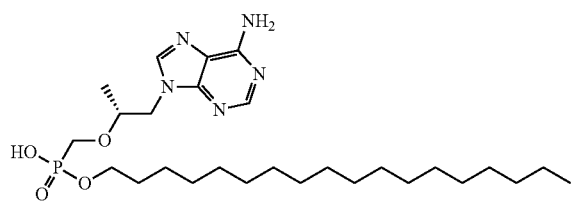 [SMILES: CCCCCCCCCCCCCCCCCCOP(=O)(O)CO[C@H](C)Cn1cnc2c(N)ncnc21]

The isolated compound of the second synthesis above was characterized by $^1$H NMR and was consistent with the presence of the desired decyl hydrogen ((((R)-1-(6-amino-9H-purin-9-yl)propan-2-yl)oxy)methyl)phosphonate. The appearance of a triplet peak at 0.855 PPM corresponded to the hydrogens of the terminal methyl group on the inserted chain and the appearance of multiple peaks at 1.26 PPM corresponded to hydrogens found in chain. The chemical structure of the prodrug is as follows:

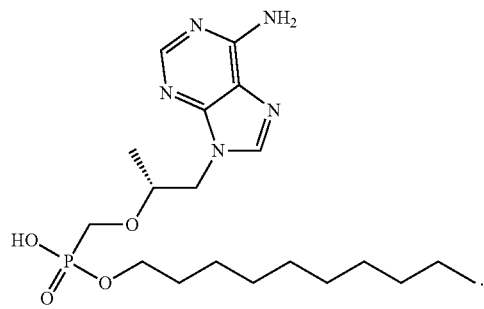 [SMILES: CCCCCCCCCCOP(=O)(O)CO[C@H](C)Cn1cnc2c(N)ncnc21]

Example 4: Tenofovir Alafenamide (TAF) Hydrogels Formed with Ascorbyl Palmitate (AP)

Methods:

Hydrogels were formed by the steps of:

(1) Adding ascorbyl palmitate (gelator) to vials 1 and 2;

(2) Adding tenofovir alafenamide (TAF), (as a co-gelator) to each the vials wherein the amount was selected to achieve a 30 wt/wt % loading of TAF in the final hydrogel;

(3) Adding a hexyl butyrate to vial 1 and propylene glycol to vial 2, such that the content of the organic solvent volume of the final volume formed was 30% vol/vol;

(4) Heating the container until dissolution of the gelator and TAF;

(5) Adding water to the container and heating the mixture until the mixture becomes a uniform solution; wherein the total volume of organic solvent and water was 200 µL; and (6) Allowing the mixture to cool to room temperature such that gelation occurs.

Results:

Hydrogels were successfully obtained when using ascorbyl palmitate as the GRAS gelator with TAF (as the free base) as the anti-retroviral co-gelator at a loading of up to 30% wt/wt using organic solvents hexyl butyrate or propylene glycol.

Optical microscopy of the hexyl butyrate hydrogel showed fibrous structures with minimal precipitates. Optical microscopy of the propylene glycol hydrogel showed organized vesicular structures. Attempts to form a hydrogel, as described above, in glycerol resulted in a hydrogel which had large precipitates when examined by microscopy.

Example 5: Maximum Loading Efficiency of
Tenofovir Alafenamide (TAF) Hydrogels Formed
with Ascorbyl Palmitate (AP)

Methods:

Hydrogels were formed according to the method described in Example 4 wherein the loading of TAF was varied (30-90% w/w) in hydrogels formed using either propylene glycol or hexyl butyrate.

Results:

It was possible to obtain TAF loadings of less than 90% w/w or less when using propylene glycol as the organic solvent in the hydrogels. It was possible to obtain TAF loadings of less than 45% w/w when using hexyl butyrate as the organic solvent in the hydrogels.

Optical microscopy of the propylene glycol hydrogels with 30% and 45% w/w TAF showed organized vesicular structures. Optical microscopy of the propylene glycol hydrogel with 60% w/w TAF showed fibrous structures with minimal precipitates. Attempts to form a hydrogel, as described above, in propylene glycol with 90% w/w TAF were not successful.

Optical microscopy of the hexyl butyrate hydrogel with 30% w/w TAF showed fibrous structures with minimal precipitates. Attempts to form a hydrogel, as described above, in hexyl butyrate with 45% w/w TAF were not successful.

Example 6: Tenofovir Alafenamide (TAF)
Hydrogels Formed with Triglycerol Monostearate
(TG18)

Methods:

Hydrogels were formed by the steps of:

(1) Adding triglycerol monostearate (gelator) to a vial;

(2) Adding tenofovir alafenamide (TAF), (as a co-gelator) to the vial wherein the amount was selected to achieve a 30 wt/wt % loading of TAF in the final hydrogel;

(3) Adding propylene glycol the vial, respectively, such that the content of the organic solvent volume of the final volume formed was 30% vol/vol;

(4) Heating the vial until dissolution of the gelator and TAF;

(5) Adding water to the mixture and heating the vial until the mixture becomes a uniform solution; wherein the total volume of organic solvent and water was 200 µL; and (6) Allowing the mixture to cool to room temperature such that gelation occurs.

Results:

A Hydrogel was successfully obtained when using triglycerol monostearate as the GRAS gelator with TAF (as the free base) as the anti-retroviral co-gelator at a loading of up to 30% wt/wt using propylene glycol as the organic solvent.

Optical microscopy of the propylene glycol hydrogel with 30% w/w TAF showed organized vesicular structures. Attempts to prepare hydrogels using hexyl butyrate and glycerol were unsuccessful.

Example 7: Maximum Loading Efficiency of
Tenofovir Alafenamide (TAF) Hydrogels Formed
with Triglycerol Monostearate (TG18)

Methods:

Hydrogels were formed according to the method described in Example 6 wherein the loading of TAF was varied (30-90% w/w) in hydrogels formed using propylene glycol.

Results:

It was possible to obtain TAF loadings of less than 45% w/w when using propylene glycol as the organic solvent in the hydrogels.

Optical microscopy of the propylene glycol hydrogel with 30% w/w TAF showed organized vesicular structures. 45% and 60% w/w propylene glycol hydrogels showed a gel with free flowing liquid and a gel having precipitates present, respectively.

Example 8: Hydrogels Formed with Ascorbyl
Palmitate (AP) with the Fumarate Salt Form of
Tenofovir Alafenamide (TAF-Fumarate)

Methods:

Hydrogels were formed by the steps of:

(1) Adding ascorbyl palmitate (gelator) to a vial;

(2) Adding the fumarate salt of tenofovir alafenamide (TAF-fumarate), (as a co-gelator) to the vial wherein the amount was selected to achieve a 30, 45, or 60 wt/wt % loading of TAF in the final hydrogel;

(3) Adding propylene glycol the vial, such that the content of the organic solvent volume of the final volume formed was 20 or 30% vol/vol;

(4) Heating the vial until dissolution of the gelator and TAF-fumarate;

(5) Adding water to the mixture and heating the vial until the mixture becomes a uniform solution; wherein the total volume of organic solvent and water was 200 µL; and (6) Allowing the mixture to cool to room temperature such that gelation occurs.

Results:

A hydrogel was successfully obtained when using ascorbyl palmitate as the GRAS gelator with TAF (as the fumarate salt form) as the anti-retroviral co-gelator at a loading of up to 30%, 45%, or 60% by wt/wt using the organic solvent propylene glycol.

Attempts to form hydrogels, as described above, with ascorbyl palmitate and hexyl butyrate or glycerol at 30%, 45%, or 60% w/w TAF (as the fumarate salt form) were not successful. Attempts to form hydrogels, as described above, with triglycerol monostearate and propylene glycol, glycerol, or hexyl butyrate at 30%, 45%, or 60% w/w TAF (as the fumarate salt form) were not successful.

Example 9: Maximum Loading Efficiency of the
Fumarate Salt Form of Tenofovir Alafenamide
(TAF-Fumarate) in Hydrogels Formed with
Ascorbyl Palmitate (AP)

Methods:

Hydrogels were formed according to the method described in Example 8 wherein the loading of TAF was varied (30-90% w/w) in hydrogels formed using propylene glycol.

Results:

It was possible to obtain TAF loadings of up to 60% w/w when using propylene glycol as the organic solvent in the hydrogels.

Example 10: Tenofovir Alafenamide (TAF) Organogels Formed with Ascorbyl Palmitate (AP)

Methods:

Organogels were formed by the steps of:

(1) Adding ascorbyl palmitate (AP) to a vials 1-5;

(2) Adding tenofovir alafenamide (TAF) (as a co-gelator) to vials 1-5, wherein the amount was selected to achieve a 30 wt/wt % loading of TAF in the final organogel;

(3) Adding olive oil to vial 1, castor oil to vial 2, corn oil to vial 3, sesame oil to vial 4, and soybean oil to vial 5;

(4) Heating the mixtures in the vials until dissolution of the ascorbyl palmitate (AP) and the tenofovir alafenamide (TAF);

(5) Allowing the mixtures in the vials to cool to room temperature such that gelation occurs, typically within 15-20 minutes.

Results:

Organogels were successfully obtained when using ascorbyl palmitate (AP) as the GRAS gelator with TAF (as the free base) as the anti-retroviral co-gelator at a loading of up to 30% wt/wt using oil-based solvents olive oil, castor oil, corn oil, sesame oil, and soybean oil.

Optical microscopy of the organogels with 30% w/w TAF formed with olive oil, corn oil, sesame oil, and soybean oil showed organized vesicular structures.

Example 11: Maximum Loading Efficiency of Tenofovir Alafenamide (TAF) in Organogels Formed with Ascorbyl Palmitate (AP)

Methods:

Organogels were formed according to the method described in Example 10 wherein the loading of TAF was varied (30-60% w/w) in hydrogels formed using olive oil, castor oil, corn oil, sesame oil, and soybean oil.

Results:

It was possible to obtain TAF loadings of less than 60% w/w when using olive oil, castor oil, corn oil, sesame oil, and soybean oil as the oil-based solvent in the organogels.

It was possible to obtain TAF loadings of at least 60% w/w when using castor oil as the oil-based solvent in the organogels.

Optical microscopy of the organogels with 30% and 45%, w/w TAF formed with olive oil showed organized vesicular structures. At 60% w/w TAF in olive oil a gel was formed which showed precipitates. Optical microscopy of the organogels with 30%, 45%, and 60% w/w TAF formed with castor oil showed no precipitates. Optical microscopy of the organogels with 30% and 45% w/w TAF formed with corn oil showed organized vesicular structures. At 60% w/w TAF in corn oil a gel was formed which showed precipitates. Optical microscopy of the organogels with 30% and 45% w/w TAF formed with sesame oil showed organized vesicular structures. At 60% w/w TAF in sesame oil a gel was formed which showed precipitates. Optical microscopy of the organogel with 30% w/w TAF formed with soybean oil showed organized vesicular structures. At 45% w/w TAF in soybean oil a gel having no precipitates was found whereas at 60% w/w TAF the gel formed showed precipitates.

Example 12: Tenofovir Alafenamide (TAF) Organogels Formed with Triglycerol Monostearate (TG18)

Methods:

Organogels were formed by the steps of:

(1) Adding triglycerol monostearate (TG18) to a vials 1-5;

(2) Adding tenofovir alafenamide (TAF) (as a co-gelator) to vials 1-5, wherein the amount was selected to achieve a 30 wt/wt % loading of TAF in the final organogel;

(3) Adding olive oil to vial 1, castor oil to vial 2, corn oil to vial 3, sesame oil to vial 4, and soybean oil to vial 5;

(4) Heating the mixtures in the vials until dissolution of the triglycerol monostearate (TG18) and the tenofovir alafenamide (TAF);

(5) Allowing the mixtures in the vials to cool to room temperature such that gelation occurs, typically within 15-20 minutes.

Results:

Organogels were successfully obtained when using triglycerol monostearate (TG18) as the GRAS gelator with TAF (as the free base) as the anti-retroviral co-gelator at a loading of up to 30% wt/wt using oil-based solvents olive oil, castor oil, corn oil, sesame oil, and soybean oil.

Optical microscopy of the organogels with 30% w/w TAF formed with olive oil, castor oil, corn oil, sesame oil, and soybean oil showed organized structures. In the case of castor oil, the structures were characterized as fibrous.

Example 13: Maximum Loading Efficiency of Tenofovir Alafenamide (TAF) in Organogels Formed with Triglycerol Monostearate (TG18)

Methods:

Organogels were formed according to the method described in Example 10 wherein the loading of TAF was varied (30-60% w/w) in hydrogels formed using olive oil, castor oil, corn oil, sesame oil, and soybean oil.

Results:

It was possible to obtain TAF loadings of less than 60% w/w when using olive oil, castor oil, corn oil, sesame oil, and soybean oil as the oil-based solvent in the organogels.

It was possible to obtain TAF loadings of at least 60% w/w when using castor oil as the oil-based solvent in the organogels.

Optical microscopy of an organogel with 30% w/w TAF formed with olive oil showed organized structures. At 45% w/w TAF the structures were vesicular structures. A 60% w/w organogel in olive oil was achieved but precipitates were present by optical microscopy. Optical microscopy of the organogels with 30% and 45 w/w TAF formed with castor oil showed fibrous structures. At 60% w/w TAF organized structures were found. Optical microscopy of the organogels with 30% and 45 w/w TAF formed with corn oil showed organized structures. A 60% w/w organogel in corn oil was achieved but precipitates were present by optical microscopy. Optical microscopy of the organogels with 30% and 45 w/w TAF formed with sesame oil showed organized structures. A 60% w/w organogel in sesame oil was achieved but precipitates were present by optical microscopy. Optical microscopy of the organogels with 30% and 45 w/w TAF formed with soybean oil showed organized structures. A 60% w/w organogel in soybean oil was achieved but precipitates were present by optical microscopy.

Example 14: Tenofovir Alafenamide (TAF) Organogels Formed with Sucrose Palmitate (SP)

Methods:
Organogels were formed by the steps of:
(1) Adding sucrose palmitate (SP) to a vial;
(2) Adding tenofovir alafenamide (TAF) (as a co-gelator) to the vials, wherein the amount was selected to achieve a 30 wt/wt % loading of TAF in the final organogel;
(3) Adding castor oil to the vial;
(4) Heating the mixtures in the vials until dissolution of the sucrose palmitate (SP) and the tenofovir alafenamide (TAF);
(5) Allowing the mixtures in the vials to cool to room temperature such that gelation occurs, typically within 15-20 minutes.

Results:
An organogel was successfully obtained when using sucrose palmitate (SP) as the GRAS gelator with TAF (as the free base) as the anti-retroviral co-gelator at a loading of up to 30% wt/wt using castor oil. Attempts to form organogels, as described above, with olive oil, corn oil, sesame oil, or soybean oil were not successful.

Optical microscopy of the organogel with 30% w/w TAF formed with castor oil showed organized structures.

Example 15: Maximum Loading Efficiency of Tenofovir Alafenamide (TAF) in Organogels Formed with Sucrose Palmitate (SP)

Methods:
Organogels were formed according to the method described in Example 14 wherein the loading of TAF was varied (30-60% w/w) in hydrogels formed using castor oil.

Results:
It was possible to obtain TAF loadings of less than 45% w/w when using castor oil as the oil-based solvent in the organogels. Attempts to form organogels with TAF loadings greater than 45% w/w in castor oil were not successful. Attempts to form organogels, as described above, with olive oil, corn oil, sesame oil, or soybean oil were not successful.

Optical microscopy of the organogel with 30% w/w TAF formed with castor oil showed organized structures.

Example 16: Organogels Formed with Ascorbyl Palmitate (AP), Triglycerol Monostearate (TG18), or Sucrose Palmitate (SP) with the Fumarate Salt Form of Tenofovir Alafenamide (TAF-Fumarate)

Methods:
Hydrogels were formed by the steps of:
(1) Adding ascorbyl palmitate, triglycerol monostearate, or sucrose palmitate (gelators) to different vials;
(2) Adding the fumarate salt of tenofovir alafenamide (TAF-fumarate), (as a co-gelator) to the vial wherein the amount was selected to achieve a 30, 45, or 60 wt/wt % loading of TAF in the final organogel;
(3) Adding castor oil the vials, such that the content of the organic solvent volume of the final volume formed was 20 or 30% by vol/vol;
(4) Heating the vials until dissolution of the gelator and TAF-fumarate;
(5) Allowing the mixture to cool to room temperature such that gelation occurs.

Results:
Organogels were successfully obtained when using ascorbyl palmitate as the GRAS gelator with TAF (as the fumarate salt form) as the anti-retroviral co-gelator at a loading of up to 30%, 45%, or 60% by wt/wt using the oil-based solvent castor oil. In the case of sucrose palmitate it was not possible to obtain an organogels at a TAF-fumarate salt loading of 45% by wt/wt. A sucrose palmitate organogels with a TAF-fumarate salt loading of 60% by wt/wt was not tested. Attempts to form organogels, as described above, with the TAF-fumarate salt in olive oil, corn oil, sesame oil, or soybean oil were not successful.

Optical microscopy of the organogel with 30% w/w TAF formed with castor oil showed organized structures.

Example 17: In Vitro Release of TAF from Hydrogels

Methods:
Two hydrogels were prepared according to the method used in Example 4 above. The hydrogels prepared were (1) 60% (w/w) TAF 30% (w/v) using ascorbyl palmitate (AP) and propylene glycol (PG); and (1) 30% (w/w) TAF 30% (w/v) using ascorbyl palmitate (AP) and propylene glycol (PG).

100 µL of the (1) 60% (w/w) TAF 30% (w/v) AP-PG and (2) 30% (w/w) TAF 30% (w/v) AP-PG hydrogels were suspended in 1.5 mL of PBS buffer containing 10% fetal bovine serum in a 100 kDa dialysis bag. The dialysis bags were placed in a sink medium (PBS) in a 50 mL falcon tube. The tubes were kept at 37° C. with shaking at 95 rpm. 1 mL aliquots were removed from the sink medium and replaced with 1 mL of fresh PBS at 0.5, 1, 2, 4, and 8 hours. The concentration of TAF in the removed aliquots was measured by HPLC to calculate the % cumulative release.

Figure 6:
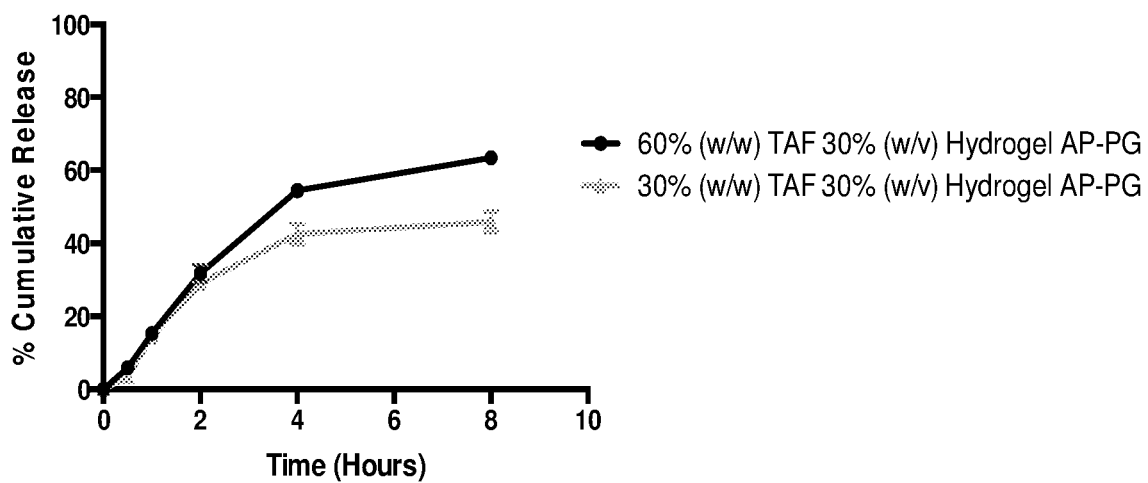
FIG. 6 is a graph showing % cumulative release (y-axis) of tenofovir alafenamide (TAF) versus time (x-axis) for two hydrogels: 60% (w/w) TAF 30% (w/v) ascorbyl palmitate (AP)-Propylene Glycol (PG); and 30% (w/w) TAF 30% (w/v) AP-PG.

Results:
As shown in FIG. 6, the % cumulative release of TAF from the hydrogels was up to about 40-60% after 8 hours.

Example 18: In Vitro Release of TAF from Organogels

Methods:
Two organogels were prepared according to the method used in Example 12 above. The organogels prepared were (1) 45% (w/w) TAF 20% (w/v) using triglycerol monostearate (TG18) and olive oil; and (1) 45% (w/w) TAF 20% (w/v) using triglycerol monostearate (TG18) and castor oil.

100 µL of the (1) 45% (w/w) TAF 20% (w/v) TG18-olive oil and (2) 45% (w/w) TAF 20% (w/v) TG18-castor oil organogels were suspended in 1.5 mL of PBS buffer containing 10% fetal bovine serum in a 100 kDa dialysis bag. The dialysis bags were placed in a sink medium (PBS) in a 50 mL falcon tube. The tubes were kept at 37° C. with shaking at 95 rpm. 1 mL aliquots were removed from the sink medium and replaced with 1 mL of fresh PBS at 0.5, 1, 2, 4, and 8 hours. The concentration of TAF in the removed aliquots was measured by HPLC to calculate the % cumulative release.

Figure 7:
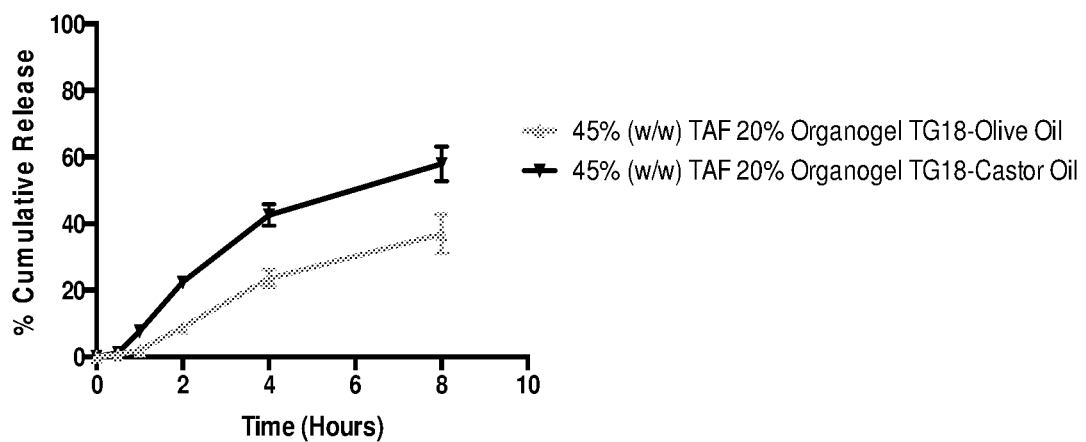
FIG. 7 is a graph showing % cumulative release (y-axis) of tenofovir alafenamide (TAF) versus time (x-axis) for two organogels: 45% (w/w) TAF 20% (w/v) triglycerol monostearate (TG18)—Olive Oil; and 45% (w/w) TAF 20% (w/v) TG18—Castor Oil.

Results:
As shown in FIG. 7, the % cumulative release of TAF from the organogels was just below 40 to just below 60% after 8 hours. The % cumulative release of TAF was found to depend upon the oil-based solvent used in the organogels.

Example 19: In Vitro Release of TAF from Organogels Co-Assembled with Cholesterol Methods:

Two organogels were prepared according to the method used in Example 12 above. The organogels prepared were (1) 60% (w/w) TAF 30% (w/v) using triglycerol monostearate (TG18) and castor oil; and (1) 60% (w/w) TAF 30% (w/v) using triglycerol monostearate (TG18) and a 50:50 weight ratio blend of cholesterol-to-castor oil.

100 µL of the (1) 60% (w/w) TAF 30% (w/v) TG18-castor oil and (2) 60% (w/w) TAF 30% (w/v) TG18-cholesterol:castor oil (50:50) organogels were suspended in 1.5 mL of PBS buffer containing 10% fetal bovine serum in a 100 kDa dialysis bag. The dialysis bags were placed in a sink medium (PBS) in a 50 mL falcon tube. The tubes were kept at 37° C. with shaking at 95 rpm. 1 mL aliquots were removed from the sink medium and replaced with 1 mL of fresh PBS at 0.5, 1, 2, 4, and 8 hours. The concentration of TAF in the removed aliquots was measured by HPLC to calculate the % cumulative release.

Figure 8:
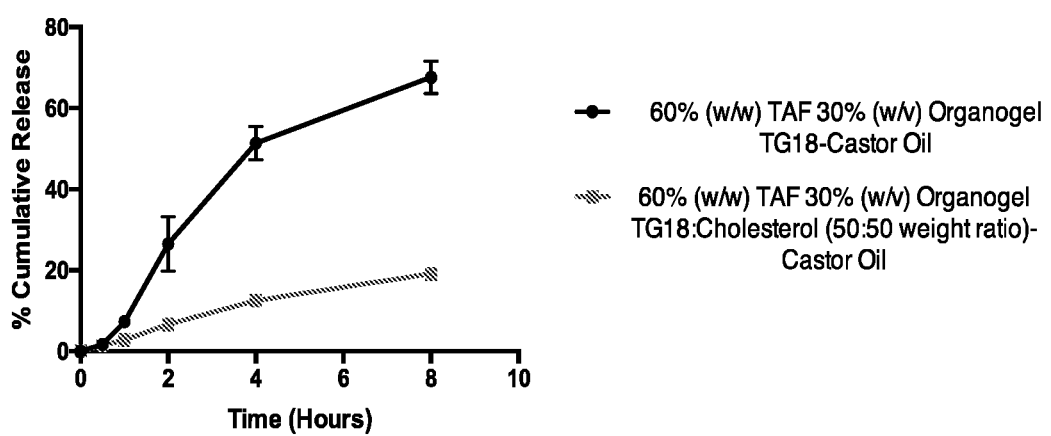
FIG. 8 is a graph showing % cumulative release (y-axis) of tenofovir alafenamide (TAF) versus time (x-axis) for two organogels: 60% (w/w) TAF 30% (w/v) triglycerol monostearate (TG18)—Castor Oil; and 60% (w/w) TAF 30% (w/v) TG18:Cholesterol (50:50 weight ratio)—Castor Oil.

Results:

As shown in FIG. 8, the % cumulative release of TAF from the organogels without cholesterol present was just about 60% after 8 hours. The % cumulative release of TAF in the organogels containing cholesterol was found to be just below about 20%. The % cumulative release was found to depend upon the presence of cholesterol in the organogels. In the case of cholesterol, it was found that addition to the organogels reduced the rate of release of TAF as compared to a gel without cholesterol.

Example 20: Stability of TAF in Hydrogels

Methods:

A hydrogel was prepared according to the method used in Example 4 above. The hydrogel prepared was 30% w/w TAF 30% w/v ascorbyl palmitate (AP) and propylene glycol.

100 µL of the 30% w/w TAF 30% w/v AP-PG hydrogel was incubated at 4° C., room temperature, and 37° C. After 1 and 4 weeks, samples of the hydrogel were dissolved in methanol and the amount of TAF was quantified.

Figure 9:
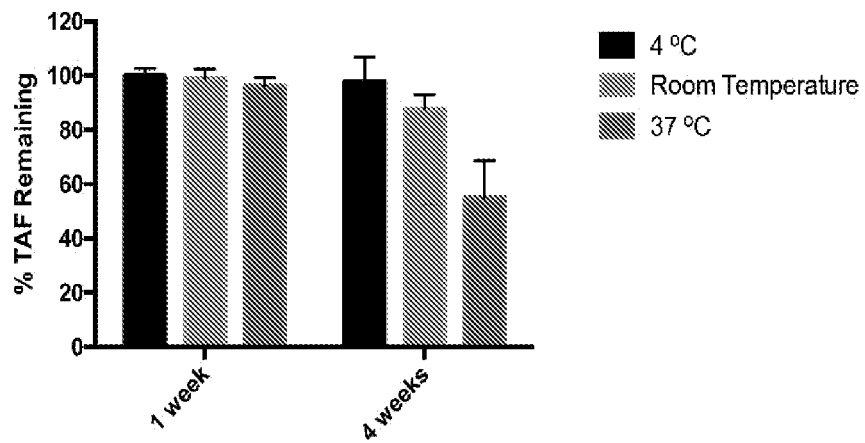
FIG. 9 is a bar graph on TAF stability in hydrogels which shows % tenofovir alafenamide (TAF) remaining (y-axis) versus time (x-axis) in hydrogels stored for 1 week and 4 weeks at 4° C., room temperature, and 37° C.

Results:

As shown in FIG. 9, the % TAF remaining from the hydrogel was essentially 100% after 1 week. After 4 weeks, the % TAF remaining in the samples stored at room temperature and 37° C. were reduced by approximately 10 and 40%, respectively.

Example 21: Stability of TAF in Organogels

Methods:

An organogel was prepared according to the method used in Example 12 above. The organogel prepared was 30% w/w TAF 30% w/v triglycerol monostearate (TG18) and olive oil.

100 µL of the 30% w/w TAF 30% w/v TG18-olive oil organogel was incubated at 4° C., room temperature, and 37° C. After 1 and 4 weeks, samples of the organogel were dissolved in DMSO and the amount of TAF was quantified.

Figure 10:
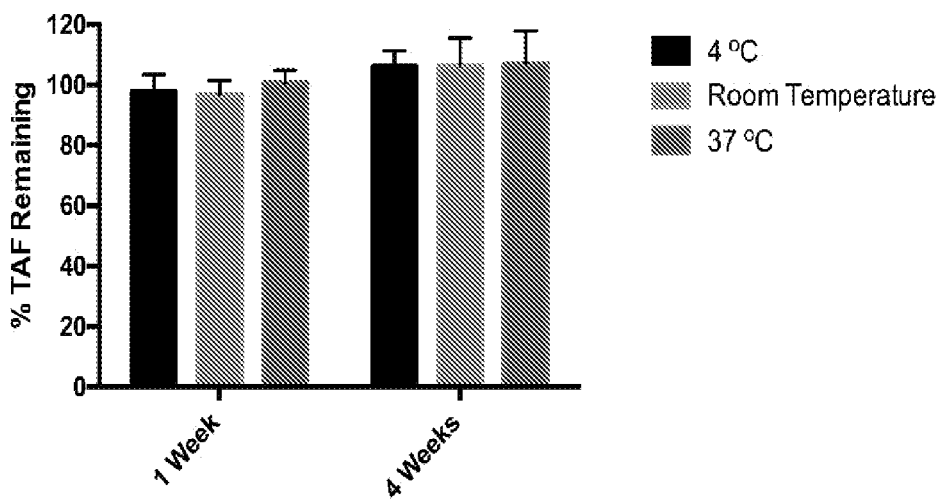
FIG. 10 is a bar graph on TAF stability in organogels which shows % tenofovir alafenamide (TAF) remaining (y-axis) versus time (x-axis) in organogels stored for 1 week and 4 weeks at 4° C., room temperature, and 37° C.

Results:

As shown in FIG. 10, the % TAF remaining from the hydrogel was essentially 100% after 1 week or 4 weeks without any degradation found in TAF under any conditions tested.

Example 22: Hydrogel Formed with Tenofovir Prodrug (Octadecyl hydrogen((((R)-1-(6-amino-9H-purin-9-yl)propan-2 yl)oxy)methyl)phosphonate)

Methods:

A hydrogel was formed by the steps of:

(1) Adding an amount of propylene glycol to a vial in an amount such that the total solvent volume in the resulting hydrogel is 25%;

(2) Adding the prodrug octadecyl hydrogen((((R)-1-(6-amino-9H-purin-9-yl)propan-2 yl)oxy)methyl)phosphonate (as a gelator; see Example 3 for synthesis) to the same vial in an amount such that the prodrug is at 6% w/v of the resulting hydrogel;

(3) Heating the mixture until dissolution of the prodrug;

(4) Adding water to the same vial in an amount such that the total solvent volume of water in the resulting hydrogel is 75%;

(5) Heating the mixture to ensure dissolution of the prodrug;

(6) Allowing the mixture to cool to room temperature such that gelation occurs, typically within 15-20 minutes.

Results:

A hydrogel was successfully obtained when using the above referenced prodrug as a gelator at a loading of 6% wt/vol and using the organic solvent propylene glycol at 25% vol/vol. Attempts to form hydrogels, as described above, with DMSO or NMP were not successful. Optical microscopy of the gel formed with propylene glycol showed no precipitates.

Example 23: Concentration Dependence of Tenofovir Prodrug (Octadecyl hydrogen((((R)-1-(6-amino-9H-purin-9-yl)propan-2 yl)oxy)methyl)phosphonate) on Formation of Hydrogels Methods:

Hydrogels were formed by the steps of:

(1) Adding an amount of NMP to vials 1-3 in an amount such that the total solvent volume in the resulting hydrogel is 25%;

(2) Adding the prodrug octadecyl hydrogen((((R)-1-(6-amino-9H-purin-9-yl)propan-2 yl)oxy)methyl)phosphonate (as a gelator; see Example 3 for synthesis) to the same vial in an amount such that the prodrug is at 6% w/v, 10% w/v, and 15% w/v of the resulting hydrogels in vials 1-3, respectively;

(3) Heating the mixture until dissolution of the prodrug;

(4) Adding water to the same vial in an amount such that the total solvent volume of water in the resulting hydrogel is 75%;

(5) Heating the mixture to ensure dissolution of the prodrug;

(6) Allowing the mixture to cool to room temperature such that gelation occurs, typically within 15-20 minutes.

Results:

A hydrogel was successfully obtained only when the above referenced prodrug, as a gelator, was present at a loading higher than 6% wt/vol and the organic solvent NMP was at 25% vol/vol. At 6% wt/vol loadings or less of prodrug no gel was obtained. The 10% wt/vol and 15% wt/vol gels showed vesicular structures with no precipitates when examined by optical microscopy.

Example 24: Organogel formed with Tenofovir
Prodrug (Octadecyl hydrogen((((R)-1-(6-amino-9H-
purin-9-yl)propan-2 yl)oxy)methyl)phosphonate)

Methods:

An organogel was formed by the steps of:

(1) Adding the prodrug octadecyl hydrogen((((R)-1-(6-amino-9H-purin-9-yl)propan-2 yl)oxy)methyl)phosphonate (as a gelator) to a vial;

(2) Adding castor oil to the vial;

(3) Heating the mixture to ensure dissolution of the prodrug;

(4) Allowing the mixture to cool to room temperature such that gelation occurs, typically within 15-20 minutes.

Results:

An organogel was successfully obtained when using the above referenced prodrug as a gelator at a loading of 6% wt/vol and using the oil-based solvent of castor oil. Attempts to form organogels, as described above, in olive oil and soybean oil were not successful The 6% wt/vol gel showed vesicular structures with no precipitates when examined by optical microscopy.

Example 25: Hydrogels Formed with Tenofovir
Prodrug (Decyl Hydrogen ((((R)-1-(6-amino-9H-
purin-9-yl)propan-2-yl)oxy)methyl)phosphonate)

Methods:

Hydrogels were formed by the steps of:

(1) Adding an amount of dimethyl sulfoxide, NMP, and propylene glycol into vials 1, 2, and 3, respectively, each in an amount that the total solvent volume in the resulting hydrogel is 25%;

(2) Adding the prodrug decyl hydrogen ((((R)-1-(6-amino-9H-purin-9-yl)propan-2-yl)oxy)methyl)phosphonate (as a gelator; see Example 3 for synthesis) to vials 1, 2, and 3, respectively in an amount such that the prodrug is at 6% w/v of the resulting hydrogel;

(3) Heating the mixture until dissolution of the prodrug;

(4) Adding water to vials 1-3 in an amount such that the total solvent volume of water in the resulting hydrogel is 75%;

(5) Heating the mixture to ensure dissolution of the prodrug;

(6) Allowing the mixture to cool to room temperature such that gelation occurs, typically within 15-20 minutes.

Results:

Hydrogels were successfully obtained when using the above referenced prodrug as a gelator at a loading of 6% wt/vol and using the organic solvents dimethyl sulfoxide, NMP, and propylene glycol at 25% vol/vol.

Optical microscopy of the formed gels showed fibrous structures with no precipitates for dimethyl sulfoxide and vesicular structures with no precipitates for NMP and propylene glycol.

Example 26: Organogel formed with Tenofovir
Prodrug (Decyl hydrogen ((((R)-1-(6-amino-9H-
purin-9-yl)propan-2-yl)oxy)methyl)phosphonate)

Methods:

An organogel was formed by the steps of:

(1) Adding the prodrug Decyl hydrogen ((((R)-1-(6-amino-9H-purin-9-yl)propan-2-yl)oxy)methyl)phosphonate (as a gelator) to a vial;

(2) Adding castor oil to the vial;

(3) Heating the mixture to ensure dissolution of the prodrug;

(4) Allowing the mixture to cool to room temperature such that gelation occurs, typically within 15-20 minutes.

Results:

An organogel was successfully obtained when using the above referenced prodrug as a gelator at a loading of 6% wt/vol and using the oil-based solvent of castor oil. Attempts to form organogels, as described above, with olive oil or soybean oil were unsuccessful.

Optical microscopy of the gel formed with castor oil showed fibrous structures with no precipitates.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A self-assembled organogel comprising
one or more gelators, wherein the one or more gelators are selected from ascorbyl palmitate, triglycerol monostearate, sucrose palmitate, alpha tocopherol acetate, cholesterol, lysophosphatidylcholine, sorbitan monostearate, retinyl acetate, retinyl palmitate, or mixtures thereof; and
one or more organic solvents, and one or more organic co-solvents, wherein the gel is treated to remove all but a residue of organic solvent.

2. The organogel of claim 1, wherein the one or more gelators are selected from the group consisting ascorbyl palmitate, triglycerol monostearate, sucrose palmitate, sorbitan monostearate, retinyl acetate, and retinyl palmitate.

3. A self-assembled organogel comprising
one or more gelators, wherein the one or more gelators are selected from ascorbyl palmitate, triglycerol monostearate, sucrose palmitate, alpha tocopherol acetate, cholesterol, lysophosphatidylcholine, sorbitan monostearate, retinyl acetate, retinyl palmitate, or mixtures thereof; and
one or more organic solvents, and one or more organic co-solvents comprising anti-viral drug selected from the group consisting of tenofovir, tenofovir alafenamide, cabotegravir, rilpivirine, emtricitabine, abacavir, lamivudine, adefovir, or combinations thereof.

4. The organogel of claim 1, wherein the one or more solvents is dimethyl sulfoxide, N-Methyl-2-pyrrolidone, isopropyl myristate, corn oil, soybean oil, castor oil, sesame oil, olive oil, 2-propanol, or mixtures thereof.

5. The organogel of claim 1, wherein the one or more gelators is ascorbyl palmitate.

6. The organogel of claim 1, wherein the one or more gelators is triglycerol monostearate.

7. The organogel of claim 3, wherein the antiviral drug co-gelator is tenofovir alafenamide or a pharmaceutical salt thereof.

8. The organogel of claim 3, wherein the one or more gelators is ascorbyl palmitate and the antiviral drug co-gelator is tenofovir alafenamide or a pharmaceutical salt thereof.

9. The organogel of claim 3, wherein the one or more gelators is triglycerol monostearate and the antiviral drug co-gelator is tenofovir alafenamide or a pharmaceutical salt thereof.

10. The organogel of claim 3, wherein the one or more gelators is sucrose palmitate and the antiviral drug co-gelator is tenofovir alafenamide or a pharmaceutical salt thereof.

\* \* \* \* \*